(12) United States Patent
McDonald

(10) Patent No.: US 12,337,169 B2
(45) Date of Patent: Jun. 24, 2025

(54) ELECTRODE ASSEMBLY AND METHODS

(71) Applicant: Baymatob Pty Ltd, Sydney (AU)

(72) Inventor: Sarah Catherine McDonald, Sydney (AU)

(73) Assignee: Baymatob Pty Ltd, Sydney (AU)

( * ) Notice: Subject to any disclaimer, the term of this patent is extended or adjusted under 35 U.S.C. 154(b) by 816 days.

(21) Appl. No.: 17/424,153

(22) PCT Filed: Jan. 24, 2020

(86) PCT No.: PCT/AU2020/050046
§ 371 (c)(1),
(2) Date: Jul. 19, 2021

(87) PCT Pub. No.: WO2020/150785
PCT Pub. Date: Jul. 30, 2020

(65) Prior Publication Data
US 2022/0096820 A1 Mar. 31, 2022

(30) Foreign Application Priority Data
Jan. 25, 2019 (AU) .................................. 2019900237

(51) Int. Cl.
*A61N 1/04* (2006.01)
*A61B 5/00* (2006.01)
*A61N 1/36* (2006.01)

(52) U.S. Cl.
CPC ........ *A61N 1/0492* (2013.01); *A61B 5/68335* (2017.08); *A61N 1/36014* (2013.01)

(58) Field of Classification Search
CPC .............. A61N 1/0492; A61N 1/36014; A61B 5/68335
See application file for complete search history.

(56) References Cited

U.S. PATENT DOCUMENTS

2011/0071611 A1 3/2011 Khuon et al.
2011/0301683 A1* 12/2011 Axelgaard ........... A61N 1/0492
607/149
2017/0333696 A1 11/2017 Shibata

FOREIGN PATENT DOCUMENTS

| CN | 108471948 A | * | 8/2018 | ........... A61B 5/0205 |
| WO | 0215974 A1 | | 2/2002 | |
| WO | 2018081819 A1 | | 5/2018 | |
| WO | 2018102874 A1 | | 6/2018 | |
| WO | WO-2019119045 A1 | * | 6/2019 | ............... A61B 5/04 |

OTHER PUBLICATIONS

PCT/AU2020/050046, "International Search Report and Written Opinion", Mar. 24, 2020, 16 pages.

* cited by examiner

*Primary Examiner* — Linda C Dvorak
*Assistant Examiner* — Abigail Bock
(74) *Attorney, Agent, or Firm* — Kilpatrick Townsend & Stockton LLP

(57) ABSTRACT

An electrode assembly including: a plurality of medical electrode members; and at least two covering sheets removably attached to the plurality of medical electrode members. The at least one covering sheet includes: a first covering sheet removably attached to one side of each of the plurality of medical electrode members; and a second covering sheet removably attached to an opposite side of each of the plurality of medical electrode members.

12 Claims, 20 Drawing Sheets

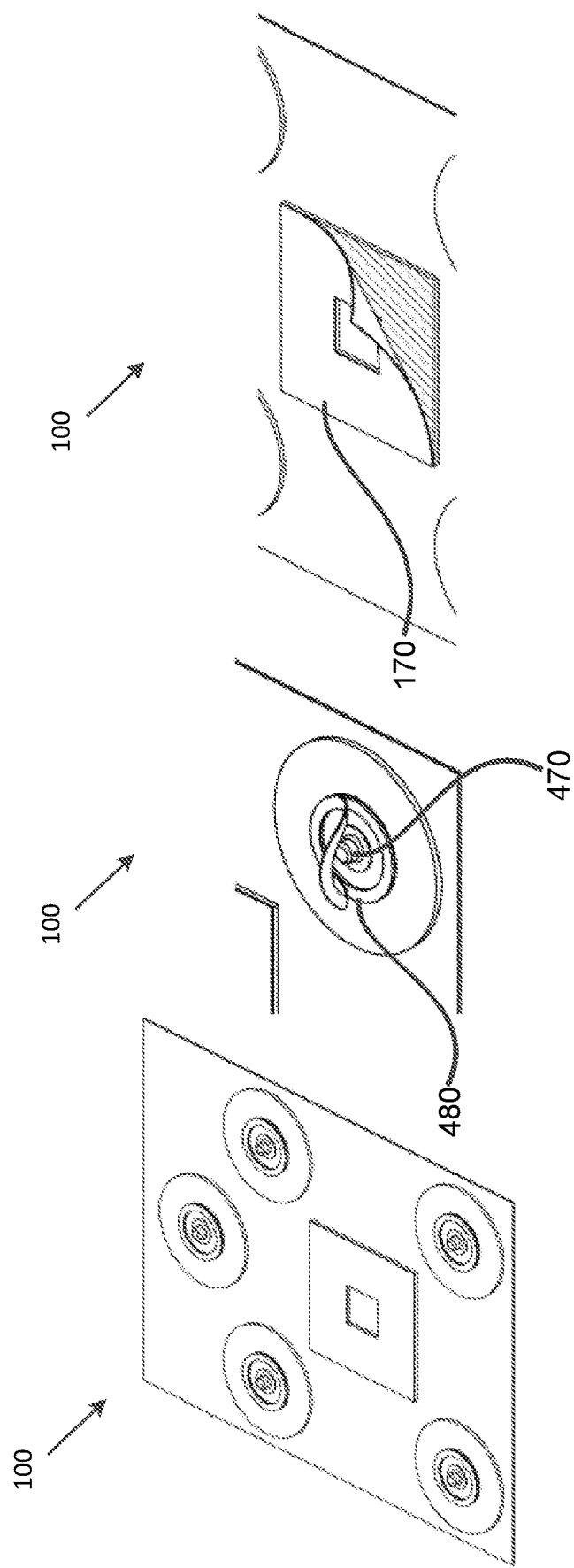

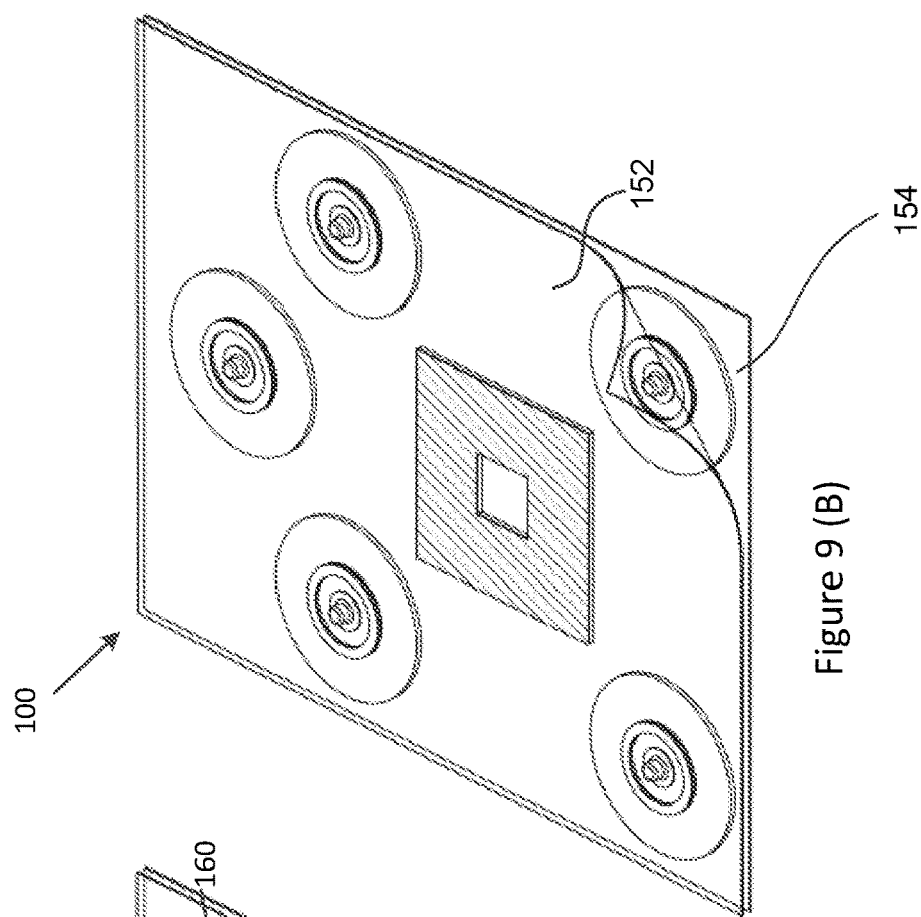
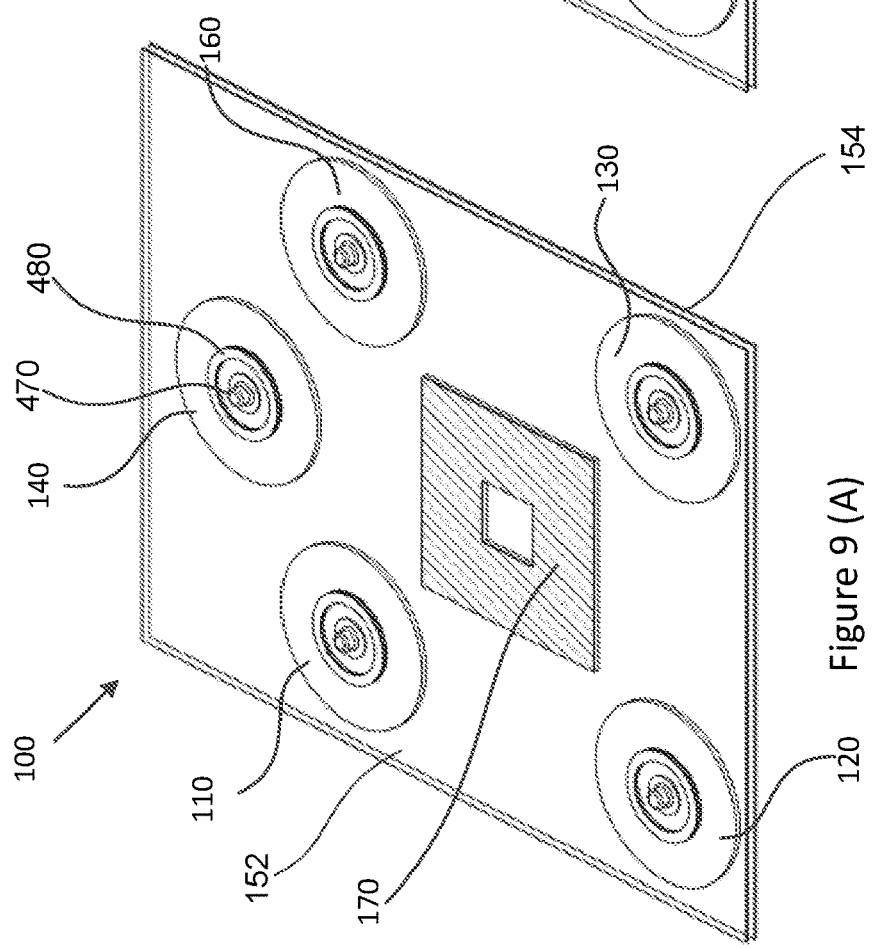

ELECTRODE ASSEMBLY AND METHODS

RELATED APPLICATIONS

This application is a U.S. National Phase of International Application No. PCT/AU2020/050046, filed Jan. 24, 2020, claiming priority to Australian Provisional Patent Application No. 2019900237, filed Jan. 25, 2019, contents of which are hereby incorporated by reference in their entirety.

TECHNICAL FIELD

The present disclosure relates to electrode assemblies and methods of using electrode assemblies.

BACKGROUND

Medical electrodes have been used in monitoring or delivering electrical signals from or to a human or animal body. Typically, a medical electrode includes a conductive member that can be placed on and electrically connected to the skin of a patient, the conductive member being also connected to an external medical device that monitors or outputs electrical signals.

Various types of medical electrodes have been developed. For example, FIGS. 13(A) and 13(B) illustrate the front side and back side views of different medical electrodes, each of which includes the following components: a connector 1310 for joining the electrode to a medical device, the connector 1310 being made of conductive material, e.g., metal; one or more flexible sheets or films 1320 for supporting the connector 1310, which may be made of e.g., cloth, plastic, foam, or any other suitable material for mechanically supporting the connector 1310 on the patient's body; a conductive area 1330, e.g., conductive gel, for electrically connecting the connector 1310 to the skin of the patient; and adhesive 1340 for securing the flexible sheet or film 1320 on the patient's body.

The adhesive 1340 may further be covered by a liner or covering, such as a flexible sheet or film that can be manually peeled off from the electrode by a user. Typically, each medical electrode is packaged separately from or can be easily separated from other medical electrodes, such that when a user applies a plurality of medical electrodes to a patient's body, each medical electrode is applied separately.

However, when multiple medical electrodes are to be applied to a patient's body or to an external medical device, applying each medical electrode separately may result in unsatisfactory accuracy of the applied positions of the medical electrodes and/or consistency in the attachment/adhesion of the electrodes, which may affect the quality of the signals captured by a medical device that monitors the electrodes, or the quality of the signals output from a medical device and delivered to the patient's body. Further, peeling off the liner from each medical electrode separately can be time consuming and inconvenient.

It is desired to address or ameliorate one or more disadvantages or limitations associated with the prior art, or to at least provide a useful alternative.

SUMMARY

In a first aspect, there is provided an electrode assembly including: a plurality of medical electrode members; and at least two covering sheets removably attached to the plurality of medical electrode members, wherein the at least one covering sheet includes: a first covering sheet removably attached to one side of each of the plurality of medical electrode members; and a second covering sheet removably attached to an opposite side of each of the plurality of medical electrode members.

In an embodiment, the at least two covering sheets are made of flexible material.

In another embodiment, the flexible material of the first covering sheet is different from the flexible material of the second covering sheet.

In yet another embodiment, each of the plurality of medical electrode members includes a first adhesive layer removably attached to the first covering sheet and a second adhesive layer removably attached to the second covering sheet.

In a non-limiting example, the first adhesive layer has different adhesive properties to that of the second adhesive layer.

In another example, the relative positions of the plurality of medical electrode members on the at least two covering sheets corresponds to the relative positions of a plurality of electrode connecting portions of a medical device.

In yet another example, the electrode assembly further comprises a non-electrode adhesive pad for holding a medical device, wherein the at least two covering sheets are also removably attached to the adhesive pad.

In an embodiment, the non-electrode adhesive pad may be arranged to form a shape selected from the group of: a circle, ellipse, triangle, square, rectangle, rhombus, trapezoid, rounded triangle, rounded square, rounded rectangle, rounded rhombus, rounded trapezoid or an irregular shape.

In another embodiment, the non-electrode adhesive pad may include an aperture arranged to form a shape selected from the group of: a circle, ellipse, triangle, square, rectangle, rhombus, trapezoid, rounded triangle, rounded square, rounded rectangle, rounded rhombus, rounded trapezoid or an irregular shape.

In yet another embodiment, the adhesive pad is located at or proximate to the centre of the at least two covering sheets.

In a non-limiting example, a device-side of the adhesive pad is spaced apart from each of the plurality of medical electrode members.

In another example, the at least one covering sheet includes at least one perforated section.

In a second aspect, there is provided a method of using an electrode assembly having a plurality of medical electrode members, the method including the steps of: removing a first covering sheet of the electrode assembly from the plurality of medical electrode members; attaching the electrode assembly to a medical device having a corresponding plurality of electrode connecting portions, such that each of the medical electrode members is secured to a corresponding one of the electrode connecting portions; removing a second covering sheet from the electrode assembly to expose the plurality of medical electrode members; and attaching the electrode assembly with the plurality of medical electrode members to a patient's body such that the plurality of medical electrode members are secured to the patient's body.

In an embodiment, the steps of removing the second covering sheet from the electrode assembly and attaching the electrode assembly with the plurality of medical electrode members to the patient's body are performed prior to the steps of removing the first covering sheet of the electrode assembly and attaching the electrode assembly to the medical device having the corresponding plurality of electrode connecting portions.

In an embodiment, the step of removing the first covering sheet of the electrode assembly exposes a first adhesive surface on each of the plurality of medical electrode members of the electrode assembly.

In another embodiment, the step of removing the second covering sheet of the electrode assembly exposes a second adhesive surface on each of the plurality of medical electrode members of the electrode assembly.

In yet another embodiment, the electrode assembly further includes a non-electrode adhesive pad for holding the medical device.

In a non-limiting example, the method further includes the step of detaching at least one perforated section of the first covering sheet and/or the second covering sheet, the at least one perforated section in removable connection with at least one of the plurality of medical electrode members, such that the perforated section can be separated from the electrode assembly so that the at least one of plurality of medical electrode members can be attached to a patient's body or a medical device.

In a third aspect, there is provided a method of using an electrode assembly, including: attaching an electrode assembly having a plurality of medical electrode members to a patient's body or a medical device; and removing at least two covering sheets of the electrode assembly from both sides the plurality of medical electrode members.

BRIEF DESCRIPTION OF THE DRAWINGS

Some embodiments of the present invention are hereinafter described, by way of example only, with reference to the accompanying drawings, wherein:

FIGS. 7 to 10 show some further examples of the electrode assembly;

FIG. 12 (B) illustrates an example of a coated paper film for covering the device-side adhesive flexible seal around a conductive connectors of a medical electrode member;

DETAILED DESCRIPTION

Multi-Electrode Assembly

Figure 1:
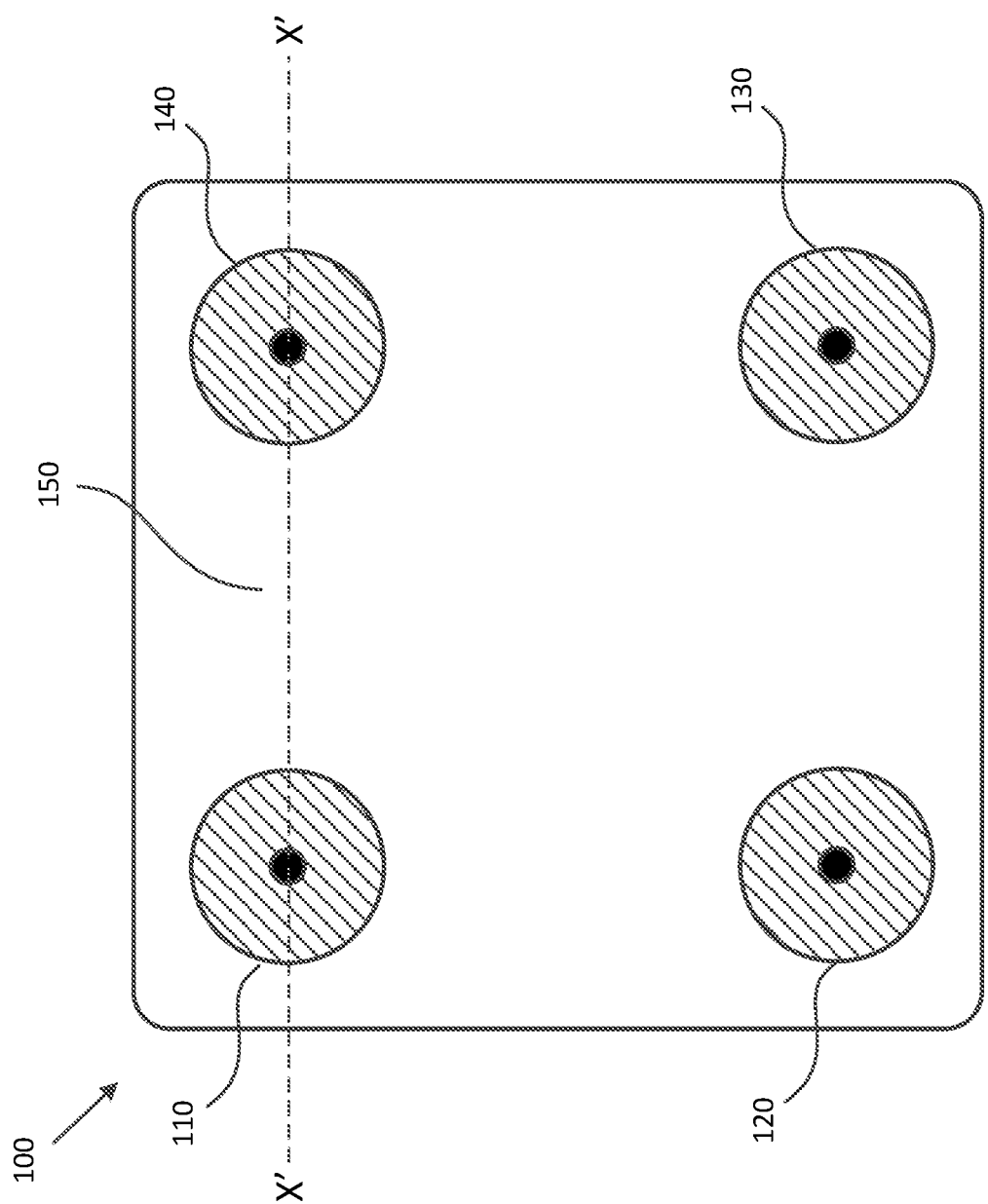
FIG. 1 illustrates an example of an electrode assembly.

Described herein is an electrode assembly 100 (also referred to as a multi-electrode assembly) that allows efficient and accurate application of multiple medical electrodes to a patient's body and/or a medical device. In the Figures, like reference numerals are used to identify like parts throughout the Figures.

Referring to FIG. 1, there is provided an example of the electrode assembly 100 (which may also be referred to as an "electrode sheet"), which includes a plurality of medical electrode members 110, 120, 130 and 140; and at least one covering sheet 150 removably attached to the plurality of medical electrode members 110, 120, 130 and 140. Each of the medical electrode members 110, 120, 130 and 140 may have the same structure as a known medical electrode device. An example of the medical electrode member 110 is shown in detail in FIG. 2. The other medical electrode members 120, 130 and 140 may have the same structure and components as the medical electrode members 110.

In this example, the medical electrode member 110 includes a flexible sheet 210 (also referred to as an "electrode backing") adaptable to the contour of the skin of a patient. The flexible sheet 210 is made of an insulating material, e.g., cloth, plastic, closed cell foam, or any other suitable insulating material that does not conduct electrically, e.g., the electrode backing material can be a foam-and-plastic combination including an adhesive flexible seal that is adhered on top of the flexible sheet 210 around an electrode connector 240. The adhesive flexible seal is described in further detail later in the specification.

An adhesive layer 220 containing a sticking substance is provided on one side of the flexible sheet 210. The adhesive layer 220 secures the flexible sheet 210 to the skin of the patient. The sticking substance is referred to as an adhesive, for example including adhesives such as but not limited to acrylic, silicone, and polyurethane based adhesives. Also provided on that side of the flexible sheet 210 is a conductive area 230. The conductive area 230 is formed of conductive substance that can electrically connect the skin of the patient with the electrode connector 240, the conductive substance being, e.g., conductive hydrophilic gel.

The electrode connector 240, may be made of a conductive material (e.g., metal) and in some embodiments may have a shape similar to a male snap fastener, or be arranged in the form of a tab, wire or custom connector, can be electrically connected, either via a flexible conductive cable (also known as a "lead") or directly, to an external medical device that monitors or generates electrical signals. It would be understood by the skilled addressee that use of various different types of known electrode connectors 240 would be understood to fall within the scope of the invention as described and defined in the claims. The electrode connector 240 as shown is merely provided as an example to demonstrate the workings of the invention, and therefore is not to be taken as limiting.

Figure 2:
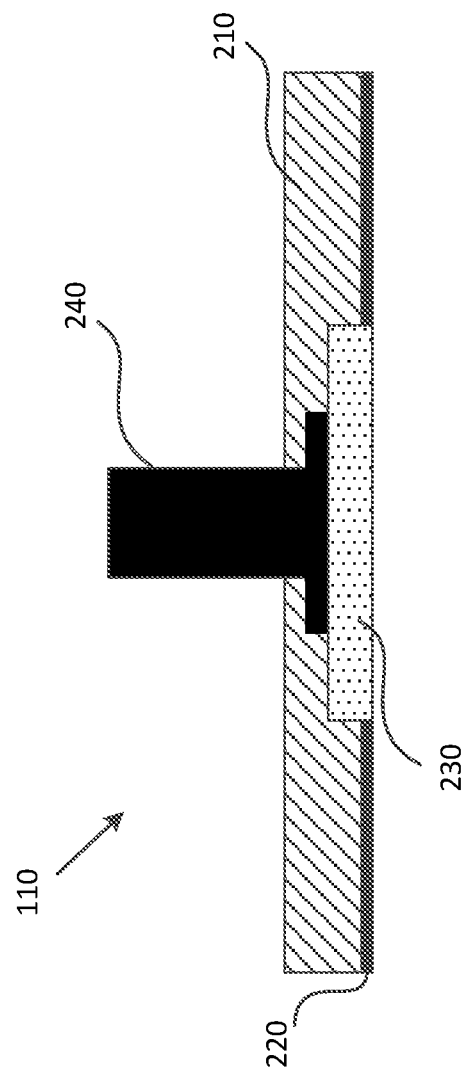
FIG. 2 illustrates an example of a medical electrode member of the electrode assembly.
Figure 3:
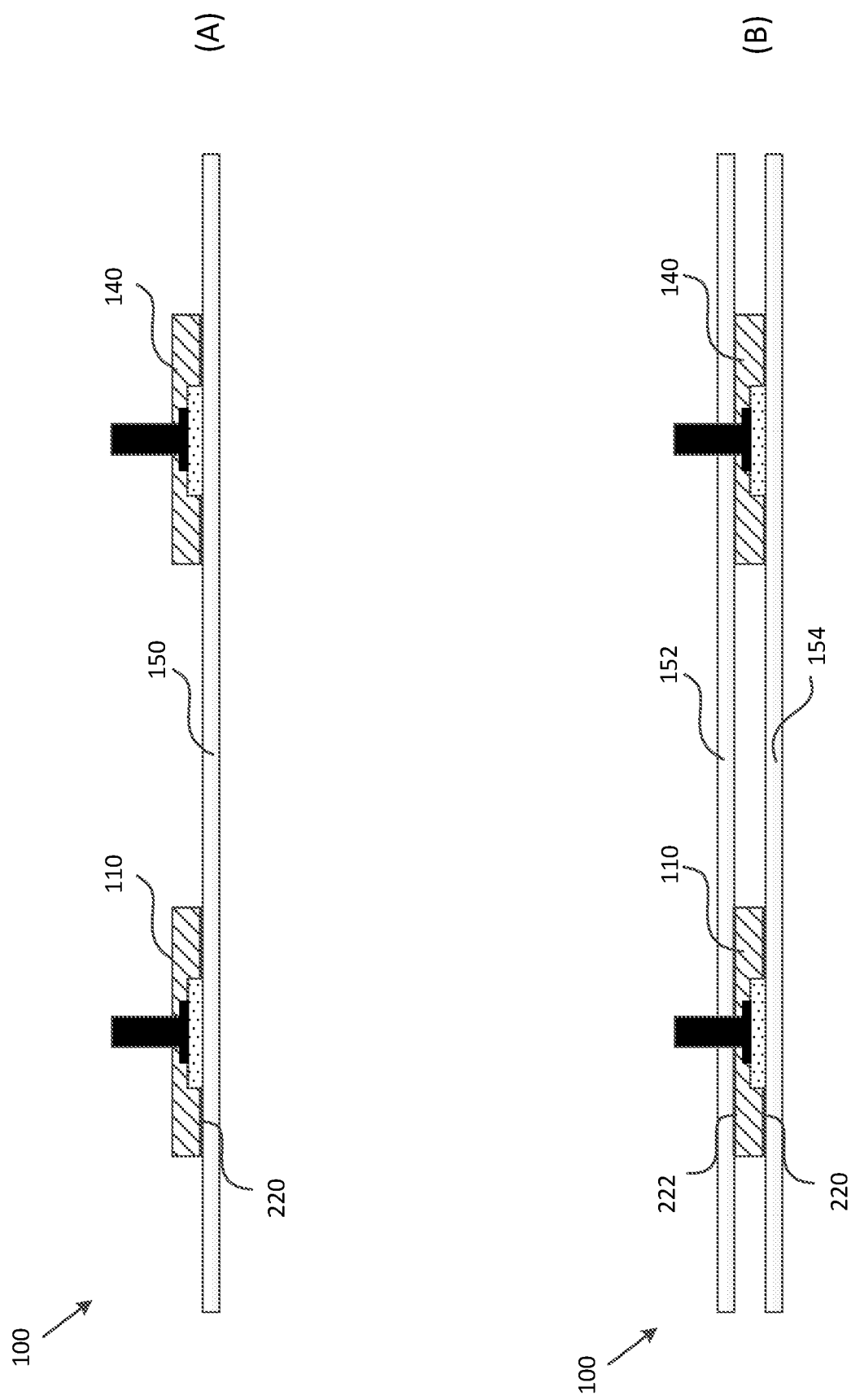
FIG. 3(A) illustrates an example of a cross-sectional view of the electrode assembly along line X'-X' in FIG. 1 with one covering sheet.
FIG. 3(B) illustrates another example of the cross-sectional view of the electrode assembly along line X'-X' in FIG. 1 with two covering sheets.
Figure 7:
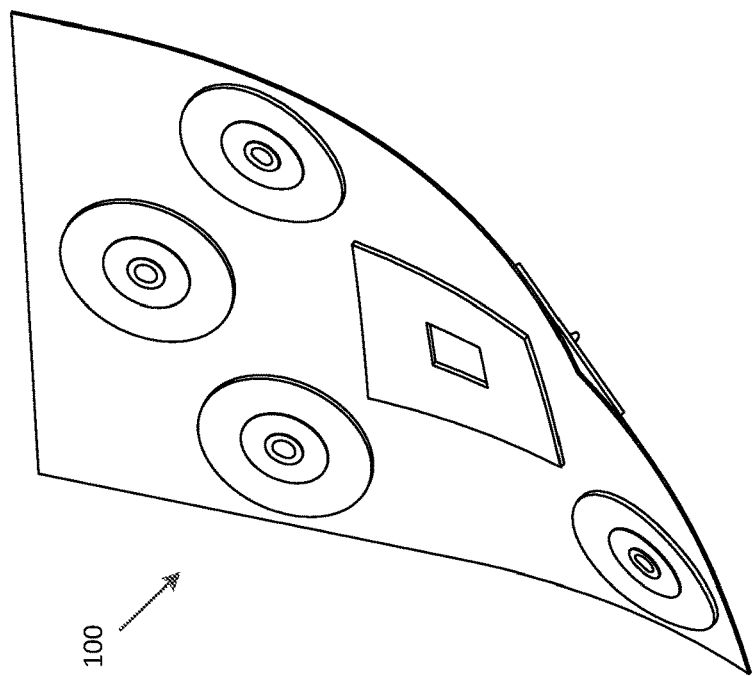
Figure 7:
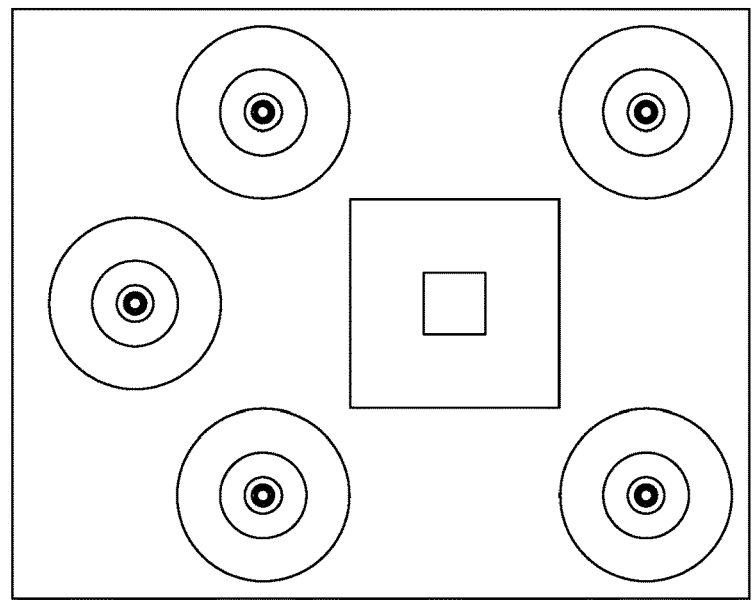

While FIG. 2 illustrates one example of the medical electrode member 110, the medical electrode member 110 may include other suitable structures and components known to a person skilled in the art, e.g., those shown in FIGS. 7(A) and 7(B). In some embodiments, one or more of the medical electrode members 110, 120, 130 and 140 may have different structures and/or components from the other medical electrode members of the electrode assembly 100. Referring now to FIG. 3(A), an example of a cross-sectional view of the electrode assembly 100 along line X'-X' in FIG. 1 is provided.

The covering sheet 150 may be arranged to removably cover the adhesive layer 220 of the medical electrode member 110, as well as the adhesive layer of the medical electrode member 140. Similarly, the covering sheet 150 removably covers the adhesive layer of each of the medical electrode members 120 and 130 (not shown). Accordingly, the covering sheet 150 (which may also be referred to as a "backing sheet", "backing film" or "liner") holds the plurality of medical electrode members 110, 120, 130 and 140 together, such that each of the medical electrode members stays in a predetermined position relative to the other medical electrode members of the electrode assembly 100. Alternatively, multiple covering sheets 150 may be used instead. For example, where a first backing sheet holds the medical electrode members 110 and 120 together and a second backing sheet holds the medical electrode members 130 and 140 together.

The covering sheet 150 may also be arranged to protect the adhesive layer of the medical electrode members during storage, and can be removed by a user (e.g., a clinician) shortly before applying the medical electrode members to the skin of the patient, so as to expose the adhesive layer. Further, the covering sheet 150 may be made from one or more flexible materials, e.g., paper, plastic, cloth, or foam, including polyester or polyethylene. In one non-limiting example, the side of the covering sheet 150 facing the medical electrode members is a smooth surface that allows easy removal from the adhesive layer of the medical electrode members.

In an embodiment, the covering sheet 150 may include at least one perforated section (not shown) to enable the at least one perforated section to be separated from the remainder of the covering sheet 150. For example, a perforated boundary may be formed on a section of the covering sheet 150, first covering sheet 152 and/or second covering sheet 154 that covers the adhesive layer for at least one of the electrode members 110. The inclusion of perforated sections in the covering sheets 150, 152 and/or 154 enables the at least one of the electrode members 110 to be removed from the rest of the covering sheet 150, whilst still keeping the adhesive layer covered and protected. For example, detaching at least one perforated section of the covering sheets 150, 152 and/or 154, where the at least one perforated section in removable connection with at least one of the plurality of medical electrode members 110, 120, 130 and 140, such that the perforated section can be separated from the electrode assembly 100 so that at least one of the plurality of medical electrode members 110, 120, 130 and 140 can be attached to a patient's body or a medical device 500. This provides improved useability by enabling at least one of the electrode members 110 to be positioned separately, for example if connected to a wire extending from the main body of a medical device, whilst the rest of the electrode members remain in position relative to one another, for example when connected to the main body of a medical device.

With reference to FIG. 3(B), another example of the cross-sectional view of the electrode assembly 100 along line X'-X' in FIG. 1 is provided. In this example, the covering sheet 150 includes a first covering sheet 152 removably attached to one side of each of the plurality of medical electrode members 110, 120, 130 and 140. Further the covering sheet 150 includes a second covering sheet 154 removably attached to an opposite side each of the plurality of medical electrode members 110, 120, 130 and 140. That is, the medical electrode members 110, 120, 130 and 140 are covered on both sides.

On one side, the second covering sheet 154 is attached to the medical electrode members 110, 120, 130 and 140 via the adhesive layer 220 of each medical electrode member. Whilst, on the other side, each medical electrode member may include a further adhesive layer 222, which is covered and protected by the first covering sheet 152.

In an example, the first and second covering sheets 152 and 154 may be made from one or more flexible materials, e.g., paper, plastic, cloth, or foam. In one non-limiting example, at least one side of each of the covering sheets 152, 154 is a smooth surface that allows easy removal from the medical electrode members. In some embodiments, one of the first and second covering sheets 152 and 154 may be formed as a plurality of separate covering sheets, each covering a medical electrode member.

Figure 4:
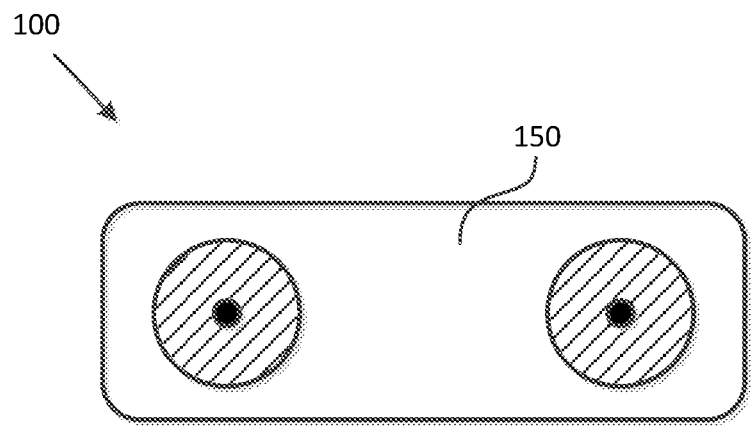
FIGS. 4(A) to 4(C) illustrate some further examples of the electrode assembly.
FIG. 4(D) shows exemplary dimensions of the electrode assembly illustrated in FIG. 4(C)
FIG. 4(E) illustrates another example of the medical electrode member.
Figure 4:
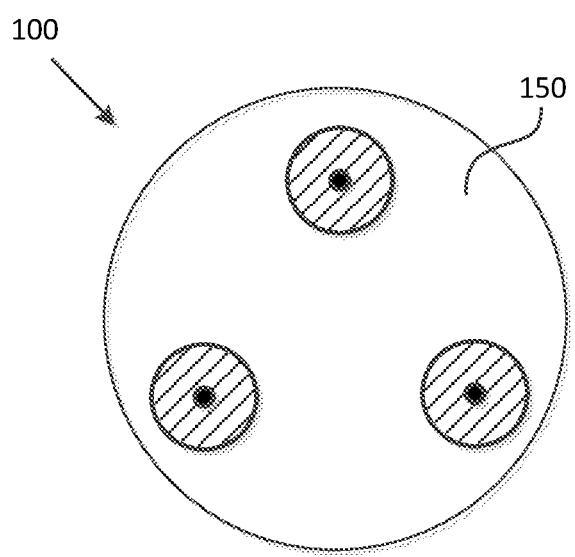
Figure 4:
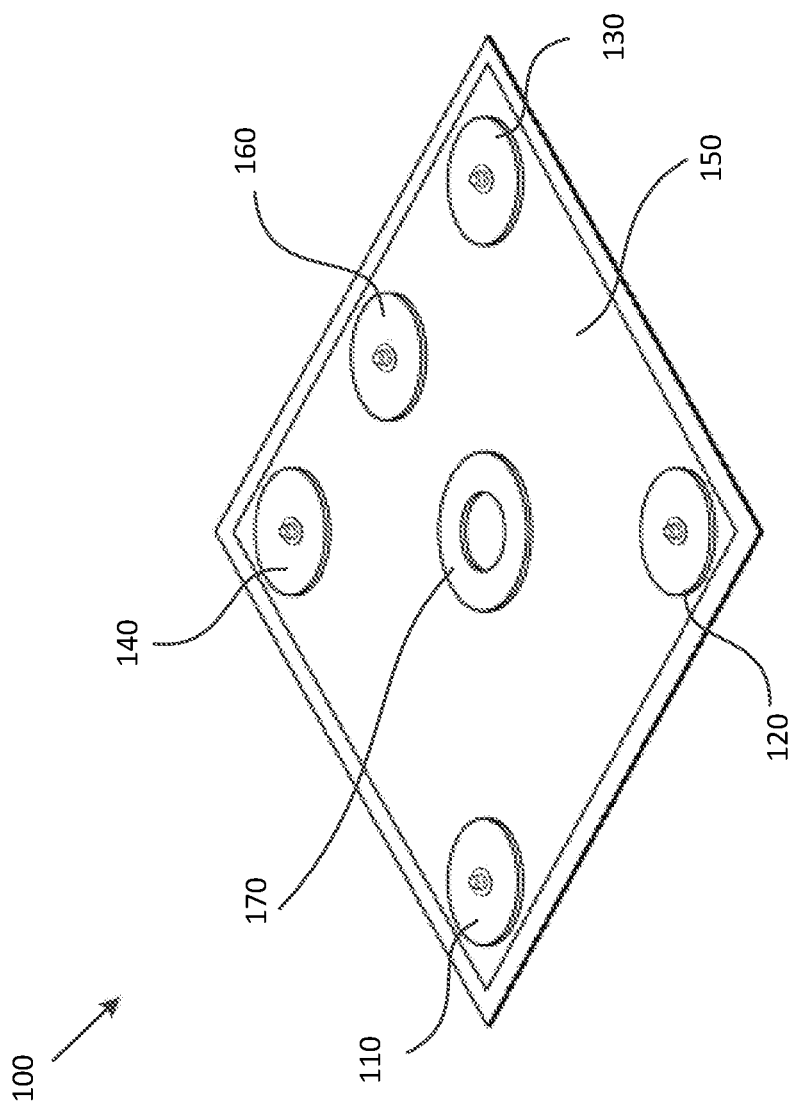
Figure 4:
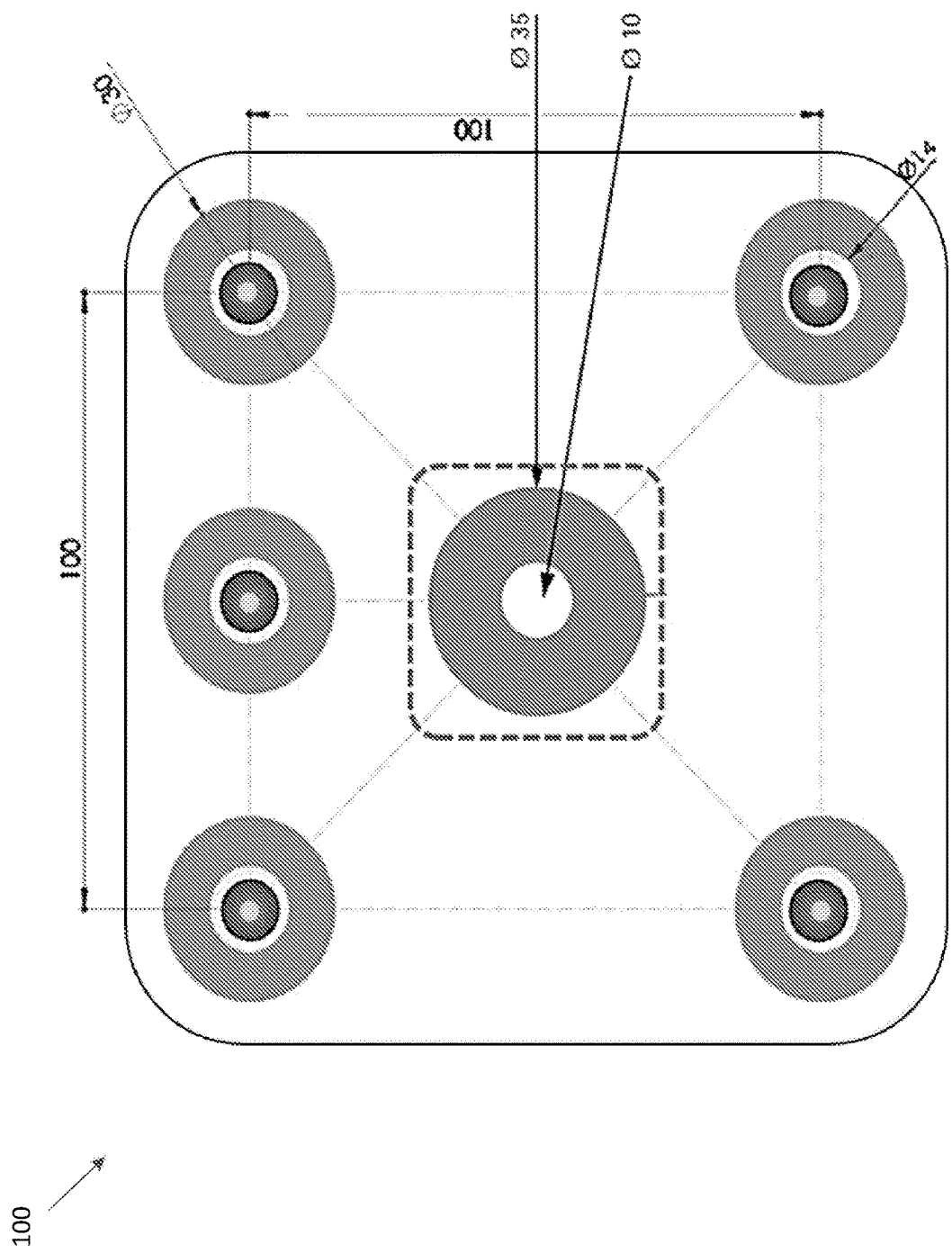
Figure 4:
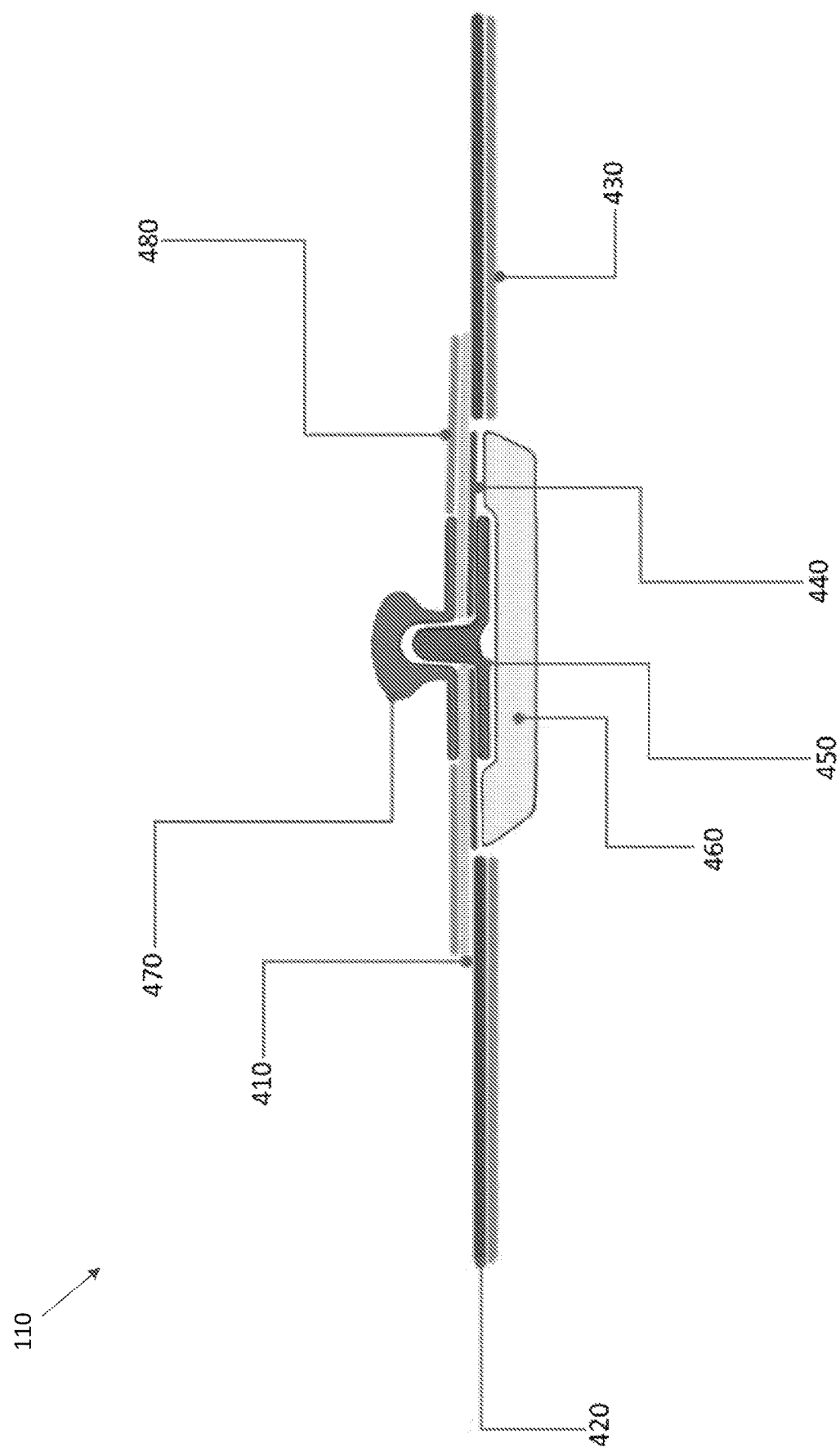

In the example shown in FIG. 1, the electrode assembly 100 includes four medical electrode members 110, 120, 130 and 140. Alternatively, the electrode assembly 100 may include a plurality of medical electrode members, as long as it is suitable for capturing signals from or sending signals to a patient's body as would be understood by the person skilled in the art. For example, in some embodiments, the electrode assembly 100 may include two medical electrode members, as shown in FIG. 4(A). In some other embodiments, the electrode assembly 100 may include three medical electrode members, as shown in FIG. 4(B).

Further, it would also be within the purview of the skilled addressee that the covering sheet may be arranged in any shape or form. For example as shown in FIG. 1, the covering sheet(s) 150 of the electrode assembly 100 has a square shape. Alternatively, the covering sheet(s) 150 may have any other shape suitable for holding the relative positions of the medical electrode members and for attaching the medical electrode members to a patient's body, e.g., rectangle, triangle, circle, polygon, an "X" shape, etc. For example, in some embodiments, the covering sheet(s) 150 may have a rectangular shape, as shown in FIG. 4(A). In some other embodiments, the covering sheet(s) 150 may have a circular shape, as shown in FIG. 4(B).

Further, in some embodiments, the electrode assembly 100 may further include a non-electrode adhesive pad (also referred to as a "non-electrode adhesive hub") that attaches to the medical device, primarily for holding the medical device to the patient. The covering sheet 150 may be removably attached to the medical electrode members and the adhesive pad, for example. as shown in FIG. 4(C).

In FIG. 4(C), the electrode assembly 100 includes a covering sheet 150 (also referred to as a "liner"), removably attached to five medical electrode members 110, 120, 130, 140, 160 and a non-electrode adhesive pad 170. The adhesive pad 170 is a shaped pad made of a material of varied pliancy. For example adhesive pad 170 may be made of a rigid, semi-rigid or flexible material. In an embodiment, the adhesive pad 170 is made from the same material as the flexible sheet 210, e.g., cloth, plastic, or closed cell foam or the same material as the covering sheets, e.g. paper, plastic cloth or foam.

The adhesive pad 170 may include an adhesive layer that is provided on one or both sides. The adhesive pad 170 can have a ring shape, or a square shape. This figure shows a non-limiting example of the electrode assembly 100 with a circular non-electrode adhesive pad. However, other embodiments, such as that shown in FIG. 7(A), provide a non-electrode adhesive pad in a square or rectangular shape. Therefore, as would be understood by the skilled addressee, the non-electrode adhesive pad may take many forms such as but not limited to a circle, ellipse, triangle, square, rectangle, rhombus, trapezoid, rounded triangle, rounded square, rounded rectangle, rounded rhombus, rounded trapezoid or an irregular shape. As would be further understood, the solid non-electrode adhesive pad may be a solid shape of any of the above shapes and may also include a gap or aperture formed in the pad that may be formed as any one of the above shapes.

In an embodiment, one side of the adhesive pad 170 can adhere to the patient's body. The opposite side of the adhesive pad 170 can adhere or securely attach to the medical device that monitors or delivers electrical signals from/to the medical electrode members of the electrode assembly 100. In this way, the adhesive pad 170 facilitates securing the medical device to the electrode assembly 100 and/or the patient's body, by supporting at least part of the weight of the medical device. This may enhance the security of the connection between the electrode assembly 100 and the medical device, and thereby improve the quality of the signals captured by/sent from the medical device.

In the example shown in FIG. 4(C), the non-electrode adhesive pad 170 is located at or proximate to the centre of the covering sheet 150. Alternatively, the non-electrode adhesive pad 170 may be located in any other location on the covering sheet 150 that allows supporting the medical device. Further, the non-electrode adhesive pad 170 may have any other shape, as long as it allows the non-electrode adhesive pad 170 to adhere to the patient's body and support the medical device on attachment. FIG. 4(D) shows exemplary dimensions of the electrode assembly 100 of FIG. 4(C).

Further, as described hereinbefore, the structure of each of the medical electrode members 110, 120, 130, 140, 160 is not limited to the example shown in FIG. 2. For instance, FIG. 4(E) illustrates another example structure of the medical electrode member 110. In this example, the medical electrode member 110 includes a substrate 410 that may be formed of cloth, plastic foam or any other suitable material for supporting a connector 470. On a patient side of the substrate 410, there is provided a flexible layer 420, wherein the flexible layer 420 is connected to the substrate 410 by means of an adhesive or other suitable engagement means. The substrate 410 may be formed of cloth, plastic foam or any other suitable material for supporting a connector 470 and may also be of a material that is adapted for contact and/or adherence to human skin (i.e. be suitable for sensitive skin). The flexible layer 420 forms at least part of the flexible sheet 210 as shown in FIG. 2. In a further embodiment, the flexible layer 420 may be breathable, where the term breathable material is understood to mean that the material layer allows for the passage of air through the layer.

The flexible material layer 420 may be connected to a patient-side adhesive layer 430 that is arranged to contact the skin of the patient. The patient-side adhesive layer 430 is arranged to attach the medical electrode 110 to the skin of the patient and support the weight of the medical electrode 110 in use. Further, the patient-side adhesive layer 430 is arranged to create a waterproof seal around an electrode sensor 450, when the medical electrode is provided to the patient.

Further, the patient side of the substrate 410 may also include a conductive printed layer 440, as such but not limited to an Ag/AgCL printed layer. In an embodiment, the conductive printed layer 440 may be directly printed onto the patient-side of the substrate 410 to deliver current to a male electrode stud connector 470 provided to a device-side of the substrate 410. Further, the conductive printed layer 440 is arranged to connect to an electrode sensor 450 and a hydro-gel layer 460, where the hydro-gel layer 460 is arranged to interface between the electrode sensor 450 and the skin of the patient.

On the device-side of the substrate 410, the male electrode stud connector 470 and the adhesive flexible seal 480 may be provided, where the substrate 410 and the conductive printed layer 440 are arranged to include an aperture that enables the electrode sensor 450 to connect directly with the male electrode stud connector 470. A device-side surface of the adhesive flexible seal 480 includes a device-side adhesive layer (not shown) that is similar to the patient-side adhesive layer, but the adhesive on the device-side of the adhesive flexible seal 480 aids in attaching the electrode assembly 100 to the medical device. The device-side adhesive layer is arranged to adhere to the underside of the medical device to create a waterproof barrier and aids with movement impact on signals. The adhesive flexible seal 480 reduces signal noise and artefacts present in the signals collected by the electrode assembly 100. Furthermore, the adhesive flexible seal 480 improves the connection of the electrode to the device and waterproofs the connection, which is particularly advantageous where the patient is moving or submerged in water.

The device-side adhesive flexible seal 480 may be of varying thickness and may be of varying shapes, such as but not limited to circular, square, triangular or another regular polygon. The adhesive flexible seal may formed of foam, plastic, adhesive gel, cloth or polymer, or another material. In an embodiment, the adhesive flexible seal 480 may may include an adhesive layer (not shown) on the device side of the adhesive flexible seal 480. The adhesive on the device-side of the adhesive flexible seal 480 aids in attaching the electrode assembly 100 to the medical device. Further, the adhesive flexible seal 480 may also include another adhesive layer (not shown) on the patient-side of the adhesive flexible seal 480 (i.e. the adhesive layer facing the substrate 410) to aid in attaching the adhesive flexible seal 480 to the substrate 410.

In one embodiment, the adhesive flexible seal 480 may comprise a thin layer of material and adhesive as shown in FIG. 4(E). Alternatively, the adhesive flexible seal may include a foam portion including a layer of adhesive provided to the device side of the adhesive flexible seal as shown in FIGS. 9(A) and 9(B).

In another non-limiting embodiment, the patient-side adhesive layer 430 and the device-side adhesive layer provided to the adhesive flexible seal 480 may include the same adhesive or bonding agent. Alternatively, the patient-side adhesive layer 430 and the device-side adhesive layer provided to the adhesive flexible seal 480 may include different adhesives or bonding agents that are optimised to suit the different properties and requirements of human skin adhesion versus adhesion to the device. This improves the use-life of the electrode, while also minimising patient discomfort.

Moreover, in another embodiment, the patient-side covering sheet provided to the adhesive layer 430 and the device-side covering sheet provided to the adhesive layer 480 may be formed from the same covering sheet material. Alternatively, the patient-side covering sheet and the device-side covering sheet may be formed from different materials to satisfy different adhesion requirements for different sized electrodes members or different adhesives as discussed above. Varying the material of the covering sheet to suit such factors reduces the risk of certain parts of the electrode assembly being pulled away from the patient-side covering sheet when the device-side covering sheet is removed.

Figure 5:
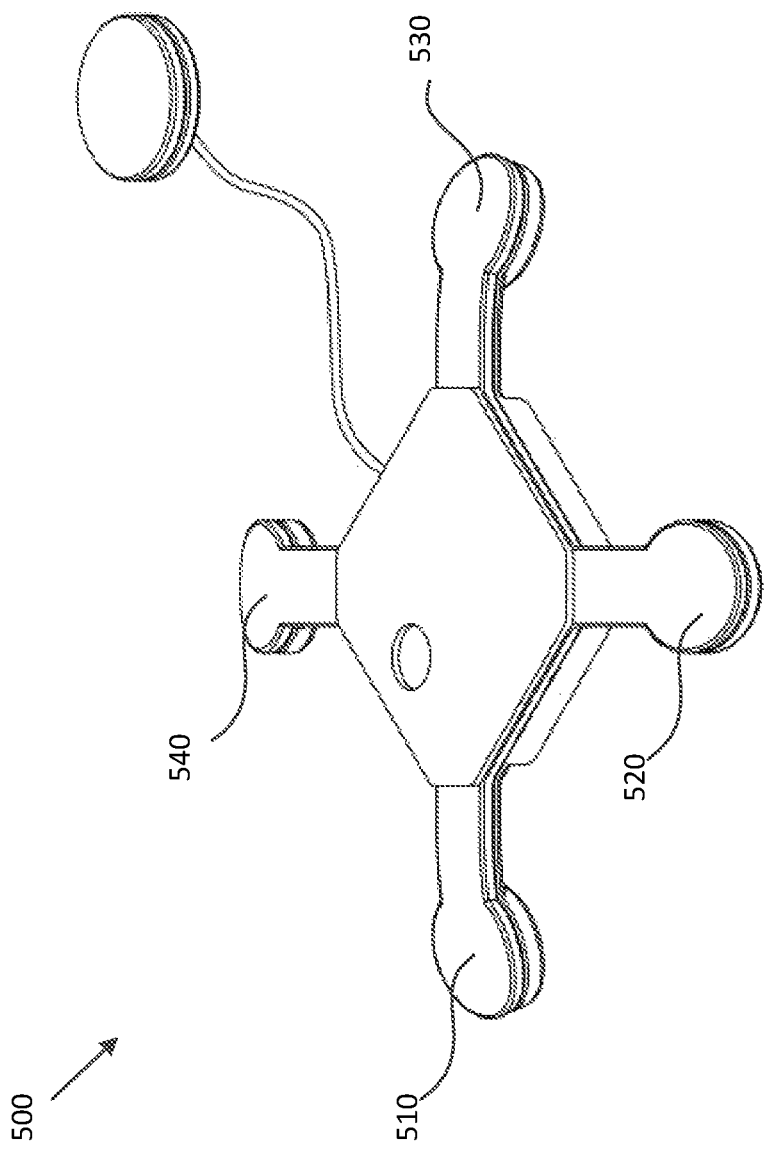
FIG. 5 illustrates an example of a medical device that can be used together with the electrode assembly shown in FIG. 1.

As mentioned hereinbefore, the electrode assembly 100 can be used together with an external medical device that monitors or delivers electrical signals from/to the plurality of medical electrode members of the electrode assembly 100. Referring now to FIG. 5 where an example is provided a medical device 500 that can be used together with the electrode assembly 100 shown in FIG. 1, e.g., the OLI™ device to which a plurality of electrode members 110 can be fastened, as described in Australian Provisional Patent Application No. 2016905046 titled "Apparatus for monitoring pregnancy or labour" and/or in PCT Application No. PCT/AU2017/051346 of the same name.

The medical device 500 includes a plurality of electrode connecting portions 510, 520, 530 and 540. Each of the electrode connecting portions is adapted to be connected to a corresponding one of the medical electrode members 110, 120, 130 and 140. Accordingly, the relative positions of the medical electrode members 110, 120, 130, 140 in the electrode assembly 100 may be arranged based on the relative positions of the corresponding electrode connecting portions 510, 520, 530 and 540 on the medical device 500. As such, it would be understood by the skilled addressee that variations to the shape and arrangement of the features of the of the corresponding electrode connecting portions 510, 520, 530 and 540 in accounting for relative positions of the medical electrode members 110, 120, 130, 140 is within the scope of the invention as described and defined in the claims.

The electrode members 110, 120, 130, 140 are mutually spaced apart in the electrode assembly 100 to mitigate mechanical and electrical interference between adjacent ones of the electrode members 110, 120, 130, 140. The electrode members 110, 120, 130, 140 are also spaced apart to connect to selected points on the skin, depending on the particular medical procedure and medical device 500. Example dimensions of the electrode assembly 100 can be about 100 millimetres (mm) between electrode members along each side, i.e., a square with sides over 100 mm. Example spacings of the electrode members 110, 120, 130, 140 can be over 50 mm centre-to-centre, e.g., 100 mm between centres, e.g., about 100 mm between centres along each side of the square arrangement in FIG. 1.

The term "patient" used in this disclosure includes both human and animal patients and users. Accordingly, the medical device 500 may include medical devices, well-being equipment and sport-monitoring equipment, for humans or veterinary devices for animals.

Method

In an embodiment, there is provided a method of using the electrode assembly 100 together with the medical device 500. Referring to FIGS. 6(A) to 6(H) illustrate an exemplary method of using the electrode assembly 100 together with the medical device 500.

Figure 6:
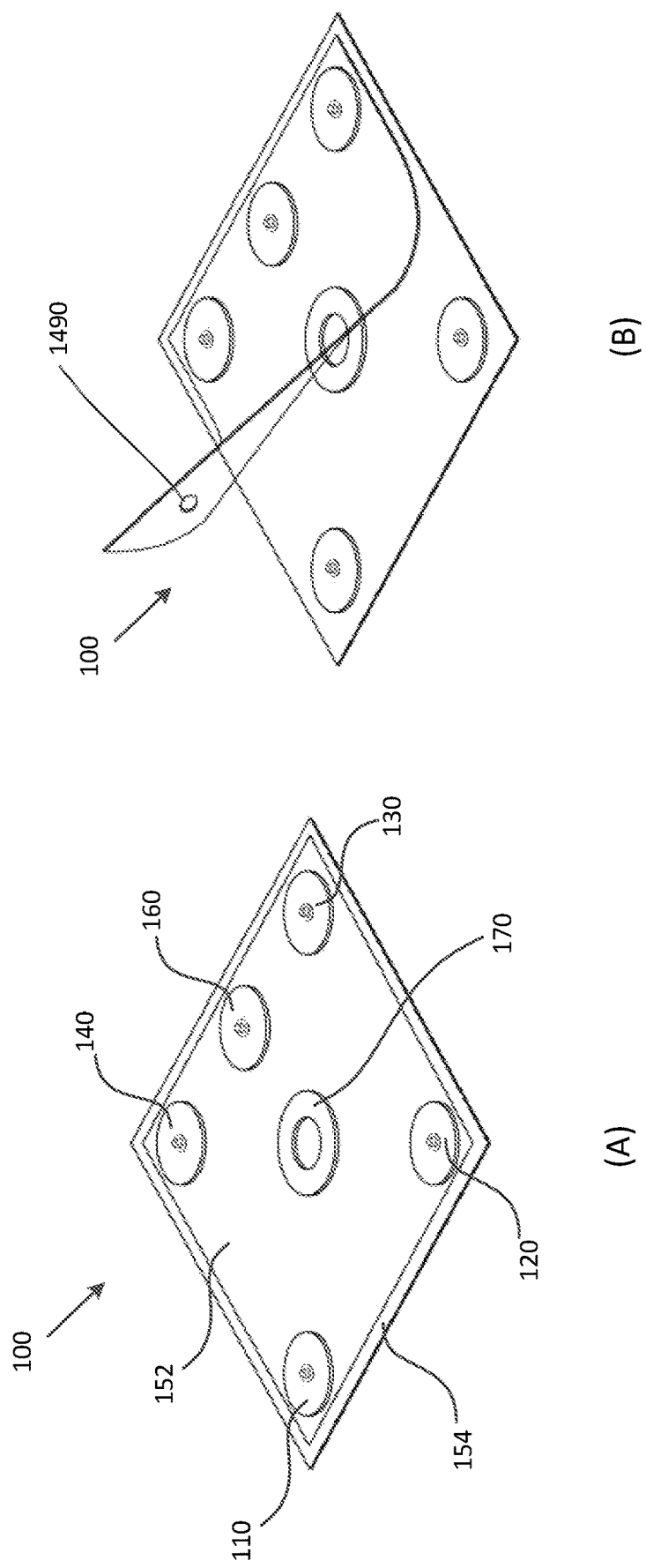
FIGS. 6(A) to 6(H) illustrate an exemplary method of using the electrode assembly together with the medical device.
Figure 6:
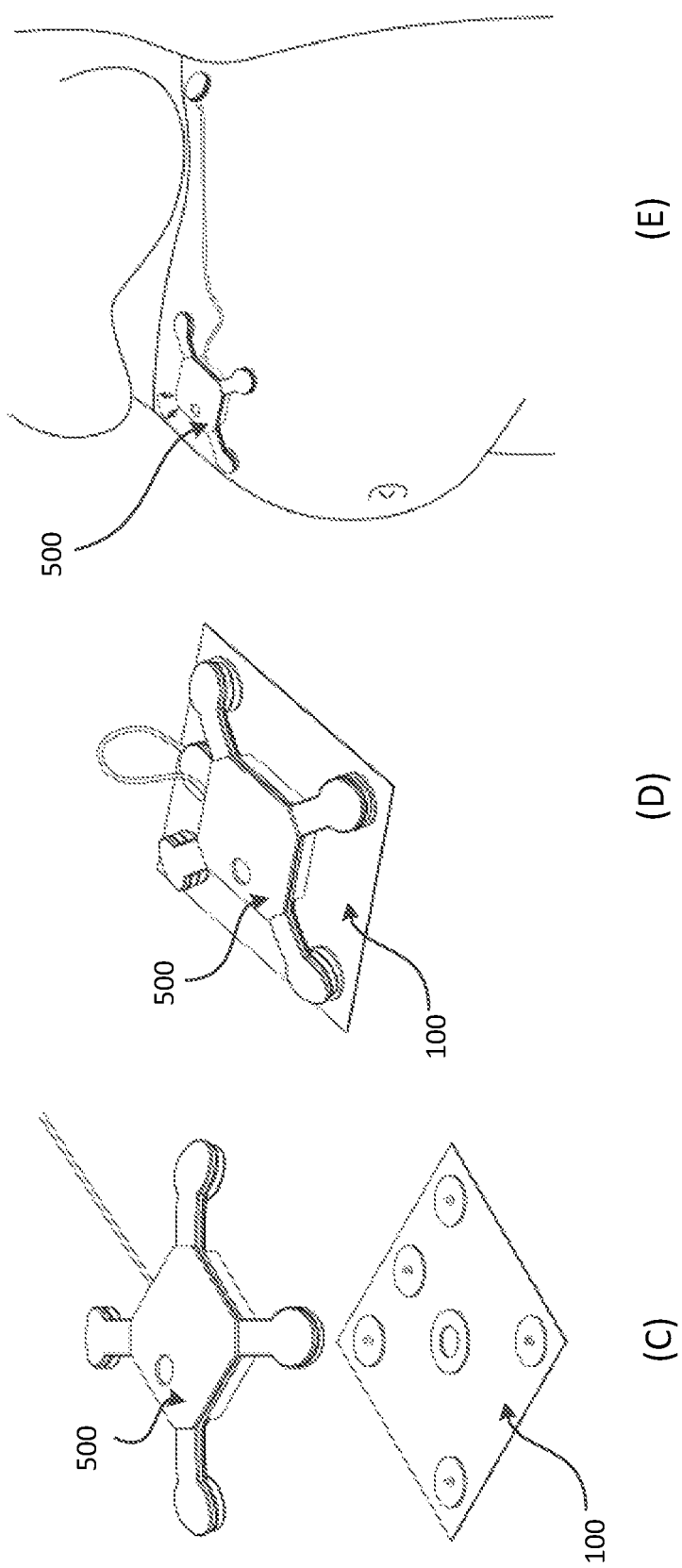
Figure 6:
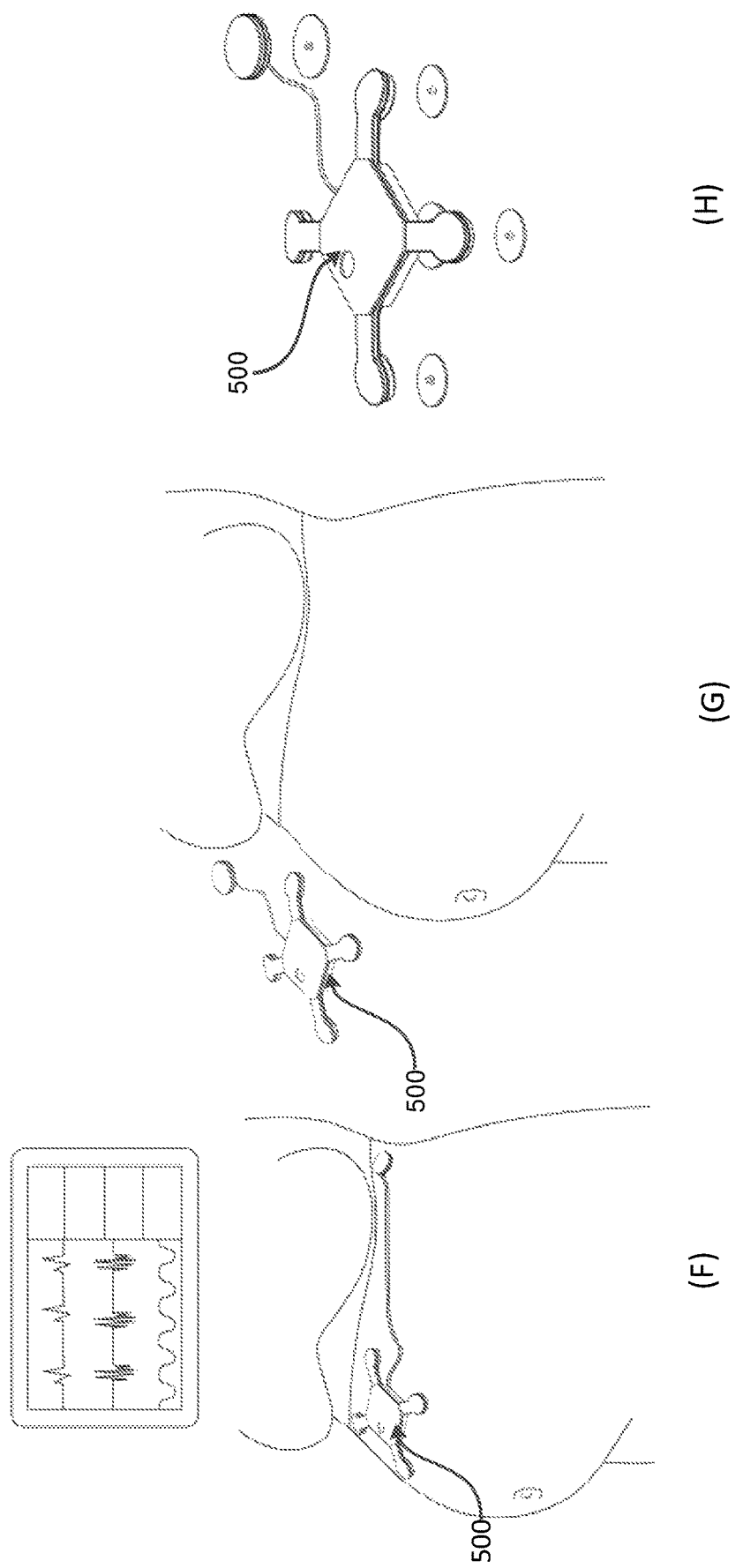

FIG. 6(A) shows the electrode assembly 100 before use. In an example, the covering sheet 150 includes the first covering sheet 152 and the second covering sheet 154. The first covering sheet 152 is removably attached to the device-side of each of the plurality of medical electrode members 110, 120, 130, 140 and 160, and the non-electrode adhesive pad 170. The second covering sheet 154 removably attached to the opposite side (patient-side) of each of the plurality of medical electrode members 110, 120, 130, 140 and 160, and the non-electrode adhesive pad 170.

In a first step, as shown in FIG. 6(B), the user peels off the first covering sheet 152 from the side of the electrode assembly 100 that is to be attached to the medical device 500. In removing the first covering sheet 152 of the electrode assembly 100 from the plurality of medical electrode members 110, 120, 130, 140 and 160, it exposes a first adhesive surface of the adhesive flexible seal 480 on each of a plurality of medical electrode members of the electrode assembly 100.

The user then attaches the electrode assembly 100 to the medical device 500, as shown in FIG. 6(C). This may occur by pressing the electrode assembly 100 and the medical device 500 together. The electrode assembly 100 may be connected to the medical device 500 so that each of the medical electrode members is secured to a corresponding one of the electrode connecting portions. The user may fasten the fastener (made of a conductive material (e.g., metal), and of a fastener type including a snap fastener (male or female), a tab, a wire or a custom connector) of the electrode connector 240 of each medical electrode member (110, 120, 130, 140 or 160) to a cooperating fastener (which is made of a conductive material (e.g., metal), and of a cooperating type to the fastener's type, e.g., a snap fastener (female or male), a tab, a wire or a custom connector respectively) on a corresponding electrode connecting portion of the medical device 500. FIG. 6(D) shows the electrode assembly 100 when connected to the medical device 500.

Alternatively or additionally, the user may adhere the flexible sheet of each medical electrode member (110, 120, 130, 140, or 160) to a flat surface on the corresponding electrode connecting portion of the medical device 500. In addition, the user may further fasten or adhere the non-electrode adhesive pad 170 to a corresponding electrode connecting portion of the medical device 500. In a further embodiment, the method may further include the step of detaching a perforated section of the second covering sheet that is connected to at least one of the plurality of medical electrode members and attaching the at least one of the electrode assembly to a patient's body or a medical device.

Next, the user peels off or removes the second covering sheet 154 from the electrode assembly 100, to expose the patient-side adhesive layer 430 of each medical electrode member (110, 120, 130, 140 or 160), and the patient-side adhesive layer of the non-electrode adhesive pad 170. The user then attaches the medical device 500 with the plurality of medical electrode members to a patient's body such that the plurality of medical electrode members are secured to the patient's body. For example, the medical device 500 with the medical electrode members 110, 120, 130, 140, 160 and the patient-side adhesive layer of the non-electrode adhesive pad 170 is applied to the patient's body as shown. The medical device 500, along with the medical electrode members 110, 120, 130, 140, 160 and the non-electrode adhesive pad 170 are secured to the patient's body through the adhesive layer of each medical electrode member and the adhesive layer of the non-electrode adhesive pad 170, as shown in FIG. 6(E).

After being secured to the patient's body, the medical device 500 and the medical electrode members 110, 120, 130, 140 and 160 can then be used to monitor or stimulate the patient, as shown in FIG. 6(F). The medical device 500 monitors the electrical signals captured by the medical electrode members 110, 120, 130, 140 and 160, or outputs electrical signals to the medical electrode members 110, 120, 130, 140 and 160 for stimulating the patient's body.

After user, the medical device 500 and the medical electrode members 110, 120, 130 or 140 can be removed from the patient's body, as shown in FIG. 6(G). The user may then remove the medical electrode members 110, 120, 130, 140, 160 and the non-electrode adhesive pad 170 from the electrode connecting portion (510, 520, 530 and 540) of the medical device 500, as shown in FIG. 6(H). The used medical electrode members 110, 120, 130, 140, 160 and the non-electrode adhesive pad 170 may be disposed after use.

Alternative Embodiments

In some other embodiments, the user may first attach the electrode assembly 100 to the patient's body before attaching the medical electrode members to the medical device 500. An example of an alternate method for attaching the electrode assembly 100 shown in FIG. 1, if the covering sheet 150 includes two covering sheet 152 and 154, the user may:

a) remove the second (patient-side) covering sheet 154 of the electrode assembly 100 to expose the plurality of medical electrode members (110, 120, 130 and 140) of the electrode assembly 100;

b) attach the electrode assembly 100 to a patient's body such that the plurality of medical electrode members (110, 120, 130 and 140) are secured on the patient's body; and c) remove the first (device-side) covering sheet 152 of the electrode assembly 100 from the plurality of medical electrode members (110, 120, 130 and 140).

d) attach the medical device 500 to the medical electrode members (110, 120, 130 and 140).

Further, in some embodiments, as shown in FIG. 1, the electrode assembly 100 may not include the non-electrode adhesive pad 170. In another embodiment as described hereinbefore, the covering sheet 150 may only include one covering sheet, which covers one side of each medical electrode member, i.e., the side with the adhesive layer 220. Accordingly, when using the electrode assembly 100, the user may:

a) attach the electrode assembly 100 to the medical device 500, such that each of the medical electrode members (110, 120, 130 and 140) is secured to a corresponding one of the electrode connecting portions (510, 520, 530 and 540);

b) remove the covering sheet 150 of the electrode assembly 100 from the plurality of medical electrode members (110, 120, 130 and 140); and c) attach the medical device 500 with the plurality of medical electrode members (110, 120, 130 and 140) to the patient's body, such that the plurality of medical electrode members (110, 120, 130 and 140) are secured to the patient's body.

According to at least some embodiments, the electrode assembly 100 described herein allows fast, easy and convenient application of a plurality of medical electrodes to a patient's body, which enhances the usability and efficiency of the electrode application process.

According to at least some embodiments, the electrode assembly 100 also ensures the medical electrodes be applied accurately to positions on the patient's body that are corresponding to the position of the electrode connecting portions on the medical device 500. This may enhance the security of the connection between the electrode assembly 100 and the medical device 500, and thereby improve the quality of the signals captured by/sent from the medical device 500.

According to at least some embodiments, the electrode assembly 100 further includes a non-electrode adhesive pad for facilitating securing the medical device 500 to the patient's body, and/or to the medical electrodes members. This may further strengthen the connection between the electrode assembly 100 and the medical device 500, and thereby improve the quality of the signals captured by/sent from the medical device 500.

EXAMPLES OF THE ELECTRODE ASSEMBLY

The following examples provide more detailed discussion of particular embodiments. The examples of the electrode assembly are shown in FIGS. 7 to 10 are intended to be merely illustrative and not limiting to the scope of the present invention as defined in the claims.

Example 1

FIG. 7(A) and FIG. 7(B) show a front view and back view respectively of an example of the electrode assembly 100 including: five medical electrode members being traditional style electrodes, with a removable covering sheet (also referred to as a "backing film") covering adhesive and hydrogel prior to application to skin. The electrode assembly 100 further includes a non-electrode adhesive pad (also referred to as a (non-electrode adhesive hub) in its centre.

The electrode assembly 100 is adapted to attach to a medical device by combination of (i) the conductive connectors (in this example press stud) of the medical electrode members, and (ii) the non-electrode adhesive hub in centre.

The electrode assembly 100 is adapted to attach to the patient's skin by combination of the medical electrode members and the non-electrode adhesive hub in centre. The non-electrode adhesive hub in the centre facilitates positioning the medical device and supporting the weight of the medical device on attachment. In this example, the non-electrode adhesive hub has a hole in centre, which allows a sensor of the medical device to protrude.

The adhesive on the side to be attached to the patient's body is protected by the removable covering sheet in the form of a plastic film. The adhesive on the opposite side of each medical electrode member and the non-electrode adhesive hub to be attached to the medical device is protected by a coated (paper) film.

Example 2

FIG. 8(A) to FIG. 8(C) show an example of the electrode assembly 100 including: five medical electrode members being traditional style electrodes with stud connectors, five respective device-side adhesive flexible seals 480 shaped as ring that are arranged to located around the stud connectors 470, and a removable covering sheet (also referred to as a "backing film") covering adhesive and hydrogel prior to application to skin. The electrode assembly 100 further includes a non-electrode adhesive pad 170 (also referred to as a "non-electrode adhesive hub") in its centre. The adhesive of the non-electrode adhesive pad 170 may be covered by a separate cover that is removed before application of the non-electrode adhesive pad 170 to the skin as shown in FIG. 8(C).

The electrode assembly 100 is adapted to attach to a medical device by combination of (i) the conductive connectors (in this example press stud) of the medical electrode members, and (ii) the non-electrode adhesive hub in its centre.

The electrode assembly 100 is adapted to attach to the patient's skin by combination of the medical electrode members and the non-electrode adhesive hub in its centre. The non-electrode adhesive hub in the centre facilitates positioning the medical device and supporting the weight of the medical device on attachment. In this example, the non-electrode adhesive hub has a hole in its centre, which allows a sensor of the medical device to protrude.

The adhesive flexible seals 480 around the conductive connectors of the medical electrode members facilitate positioning of the medical device, reducing movement artefacts, and preventing fluid ingress. The adhesive on the side to be attached to the patient's body is protected by the removable covering sheet in the form of a plastic film. The adhesive on the opposite side of each medical electrode member (i.e., the medical device side) and the non-electrode adhesive hub to be attached to the medical device is protected by a coated (paper) film.

Example 3

FIG. 9(A) and FIG. 9(B) show an example of the electrode assembly 100 including: five medical electrode members 110, 120, 130, 140 and 160, each being traditional style electrodes and each having a respective adhesive flexible seal 480 around the stud connectors 470, and two removable covering sheets 152, 154 (also referred to as "backing films"). The electrode assembly 100 further includes a non-electrode adhesive pad 170 (also referred to as a "non-electrode adhesive hub") in its centre.

One of the removable covering sheets 154 covers adhesive and hydrogel prior to application to skin. The other removable covering sheet 152 covers the non-electrode adhesive hub in centre and the adhesive flexible seals 480. The electrode assembly 100 is adapted to attach to a medical device by combination of (i) the conductive connectors (in this example press stud) of the medical electrode members, and (ii) the non-electrode adhesive hub in centre.

Further, the electrode assembly 100 is adapted to attach to the patient's skin by combination of the medical electrode members 110, 120, 130, 140 and 160 and the non-electrode adhesive hub 170 in its centre. The non-electrode adhesive hub 170 in the centre facilitates positioning the medical device and supporting the weight of the medical device on attachment. In this example, the non-electrode adhesive hub 170 has a hole in its centre, which allows a sensor of the medical device to protrude.

The device-side adhesive flexible seal 480 is arranged around the conductive connectors 470 of each of the medical electrode members 110, 120, 130, 140 and 160 to aid in positioning the medical device, reducing movement artefacts, and preventing fluid ingress. The adhesive on the side to be attached to the patient's body is protected by one of the removable covering sheets, taking the form of a plastic film. Meanwhile, the adhesive on the opposite side of the non-electrode adhesive hub 470 and adhesive flexible seal 480 that is to be attached to the medical device is covered and protected by the other removable covering sheet 152 in the form of a plastic film.

Example 4

Figure 10:
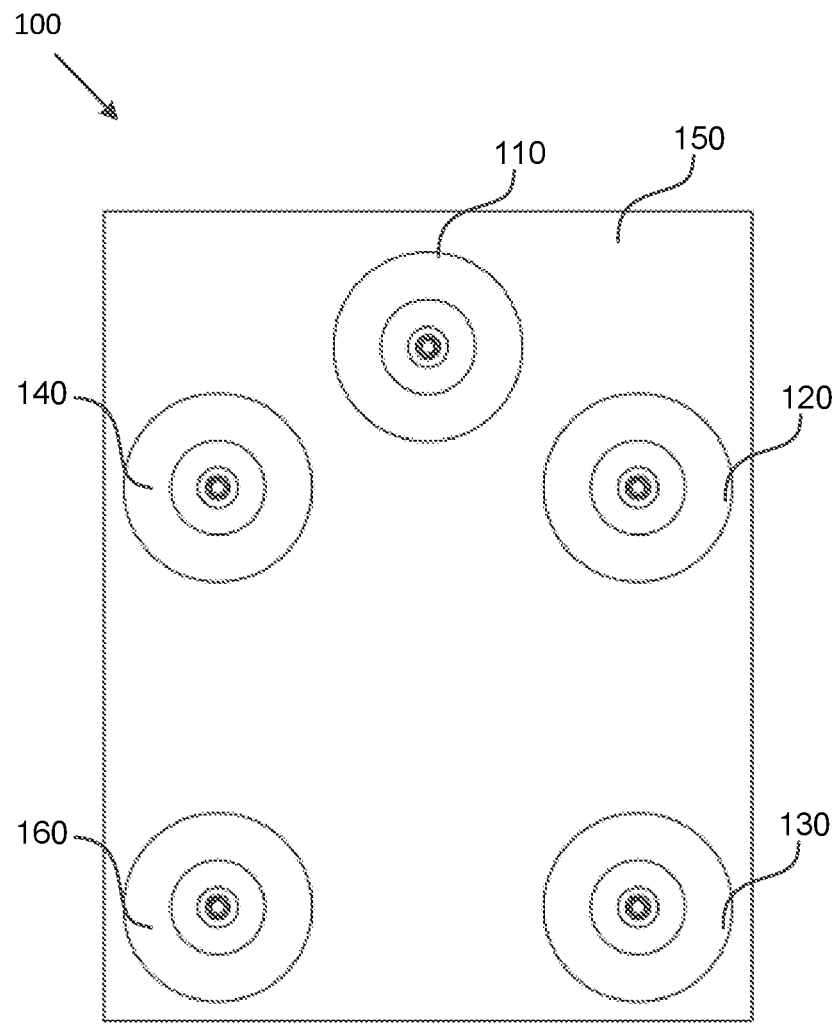

FIG. 10 shows an example of the electrode assembly 100 including: five medical electrode members 110, 120, 130, 140 and 160 being traditional style electrodes, and a single removable covering sheet 150 (also referred to as a "backing film") covering adhesive and hydrogel prior to application to skin. In this example, the electrode assembly 100 does not include the non-electrode adhesive pad.

The electrode assembly 100 is adapted to attach to a medical device by the conductive connectors (in this example press stud) of the medical electrode members. The electrode assembly 100 is adapted to attach to the patient's skin through the adhesive on one side of the medical electrode members, the adhesive being covered by a single removable covering sheet.

In the above-described Examples 2 and 3, the device-side adhesive flexible seals 480 around the conductive connectors of the medical electrode members are raised from the surface with a foam layer. This configuration may provide a better performance of positioning the medical device, reducing movement artefacts, and/or preventing fluid ingress under movement of the patient's body or the medical device. However, in some embodiments, the device-side adhesive flexible seal 480 may be a thin film and adhesive that sits flush with the surface of the electrode. In some other embodiments, adhesive flexible seal 480 may have a thicker layer that increases the distance between the substrate 410 connecting surface of the adhesive flexible seal 480 and the medical device contacting surface of the adhesive flexible seal 480. As aforementioned, instead of using a foam layer, the adhesive flexible seal 480 may be a layer of adhesive gel, cloth or polymer.

Figure 11:
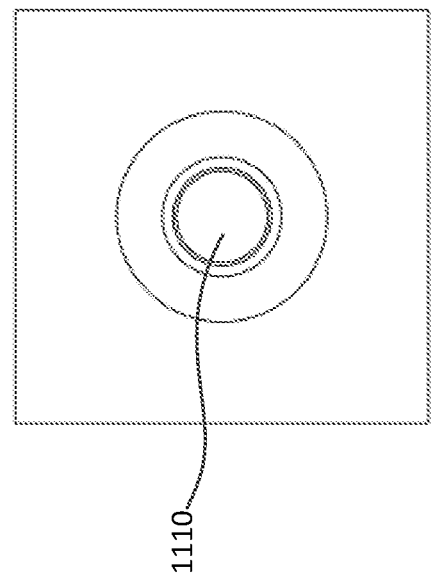
FIG. 11(A) and FIG. 11(B) illustrate an example of a film backing for a medical electrode member with a cup.
Figure 11:
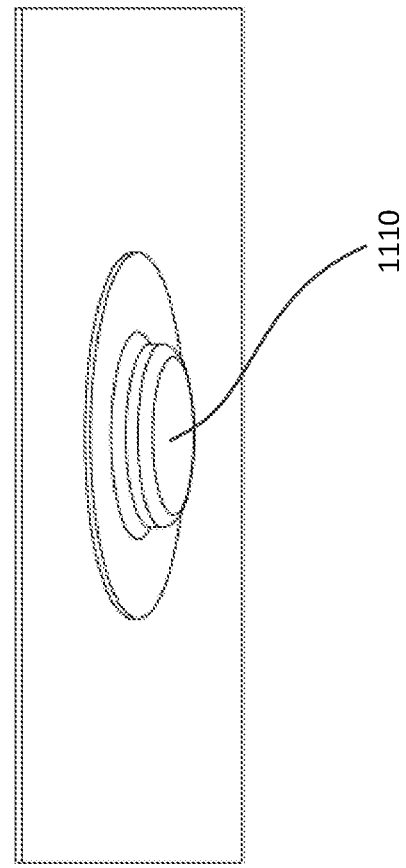

Referring to FIG. 11(A) and FIG. 11(B), there is provided an example of an alternative removable covering sheet ("film backing"), which includes a cup 1110 for each electrode (as opposed to flush plastic as shown in FIGS. 8 and 9). The cup 1110 can contain hydrogel and cover the conductive connector's surface that attaches to the medical device. The covering sheet that includes the cups 1110 can include various types of plastics or coated papers.

Figure 12:
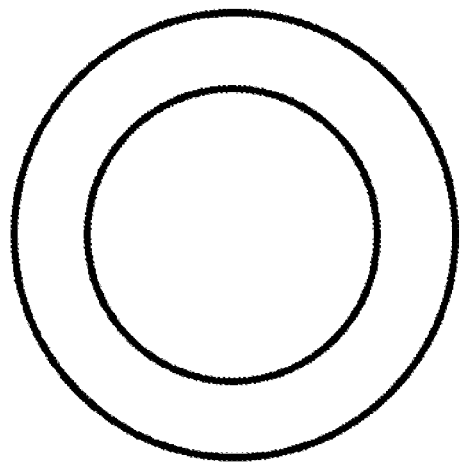
FIG. 12 (A) illustrates an example of a coated paper film for covering the non-electrode adhesive pad.
Figure 12:
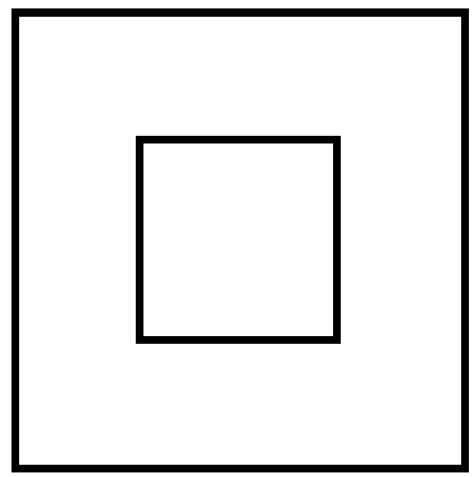
Figure 13:
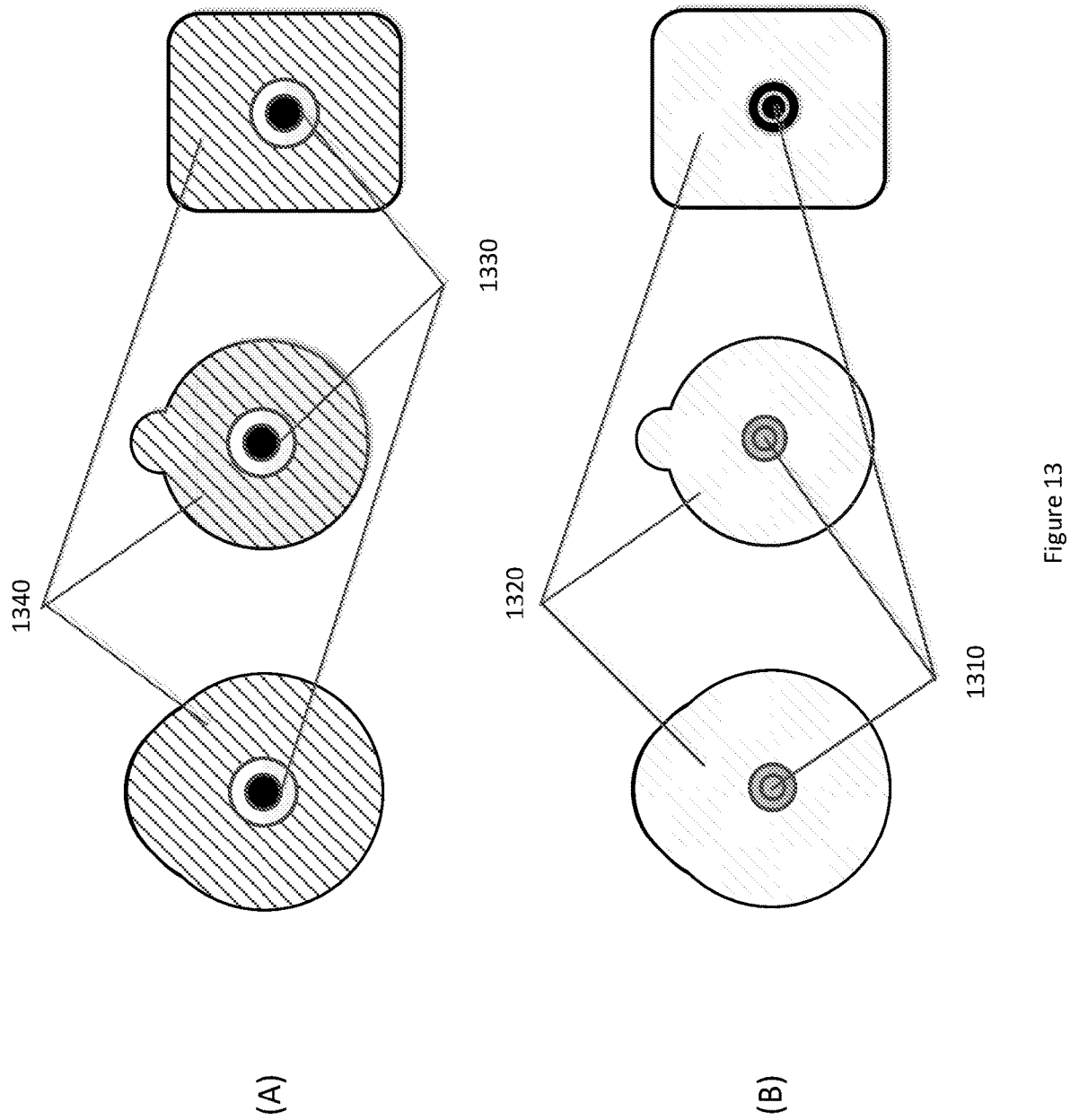
FIGS. 13(A) and 13(B) illustrate the front side and back side views of different medical electrodes.

Referring now to FIG. 12 (A) an example of a coated paper film for covering a non-electrode adhesive pad is provided. FIG. 12 (B) illustrates an example of a coated paper film for covering the foam ring-shaped adhesive flexible seal that is arranged around a conductive connector of a medical electrode member, which is shown being removed in FIG. 8(B).

Example 5

Figure 14:
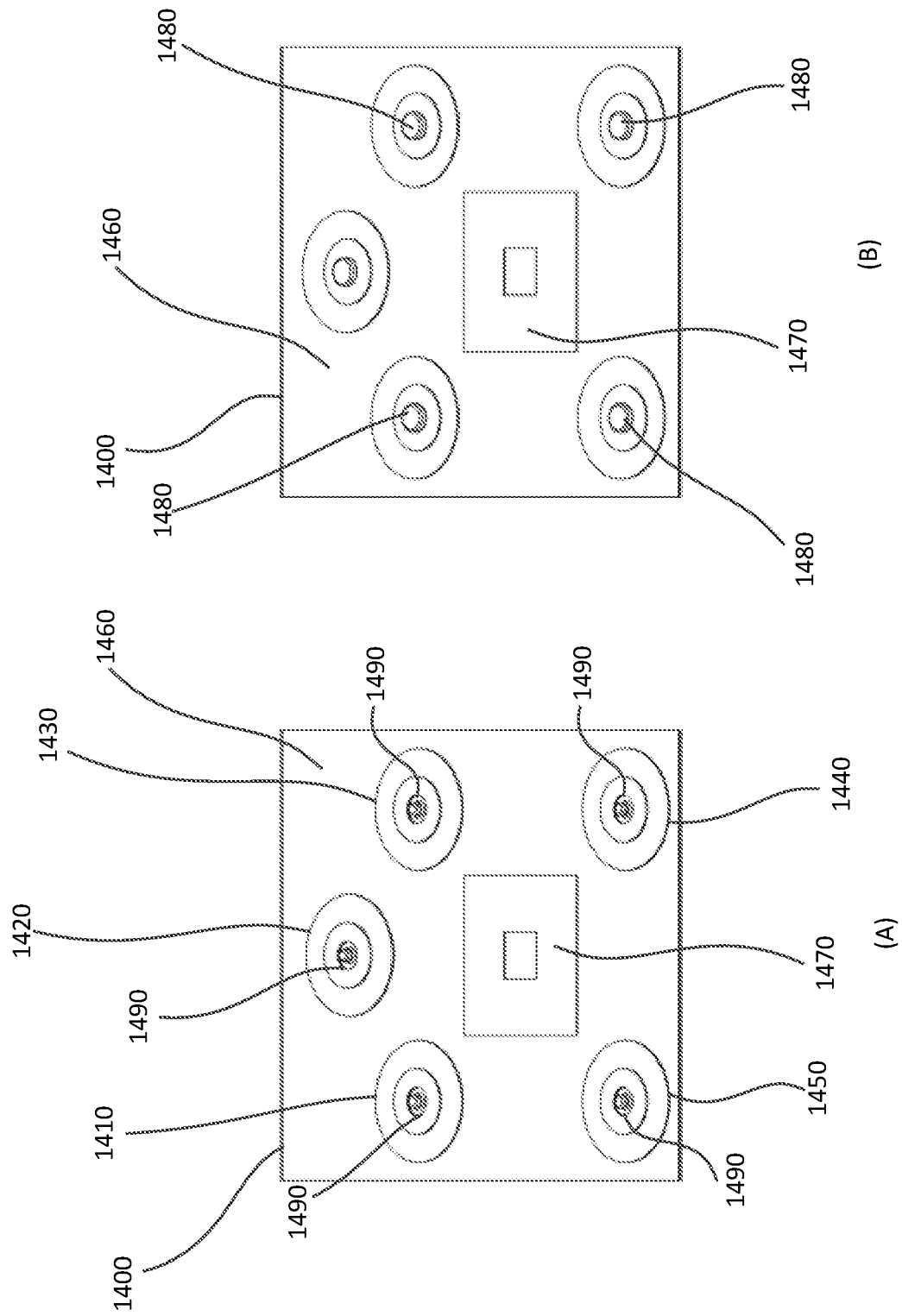
FIG. 14(A) to 14(C) illustrate a further example of the electrode assembly.
Figure 14:
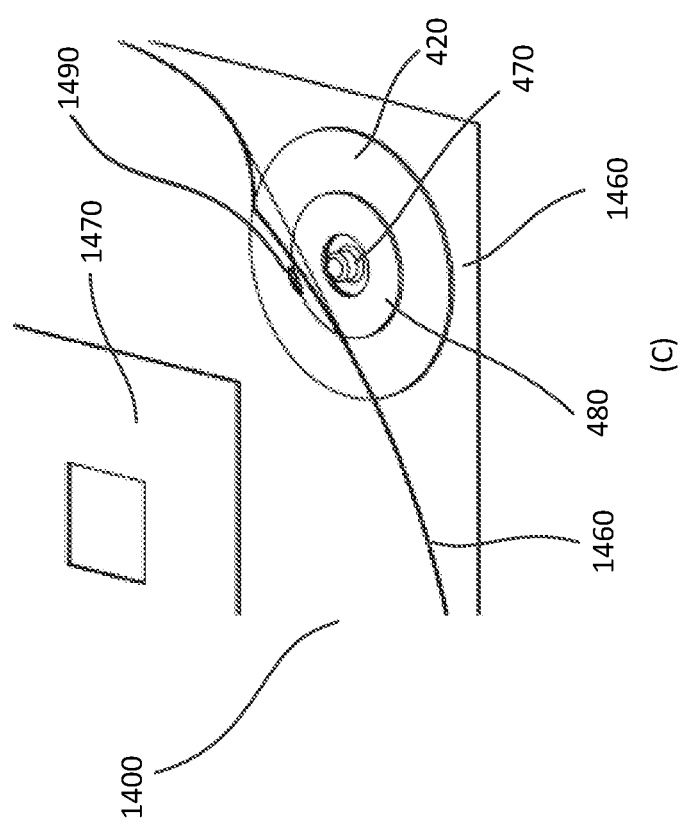

FIGS. 14(A), (B) and (C) show an example of an electrode assembly 1400 including: five medical electrode members (1400, 1420, 1430, 1440, 1450) each being traditional style electrodes with electrode connectors 470 including stud connectors, and two removable covering sheets 1460 (also referred to as "backing films") provided to each side of the electrode members. The electrode assembly 1400 further includes a non-electrode adhesive pad 1470 (also referred to as a "non-electrode adhesive hub") in its centre. FIG. 14(A) is a front view, FIG. 14(B) is a back view and FIG. 14(C) is a detailed front view.

One of the removable covering sheets 1460 on the patient-side covers the patient-side adhesive layer 430 and a hydrogel layer 460 prior to application to skin. The hydrogel layer 460 is contained within a plurality of concave deformations 1480 formed in the patient-side covering sheet 1460. The deformations 1480 function in a similar manner to the aforementioned cups 1110, however the deformations 1480 are integrally formed with the patient-side covering sheet 1460.

The device-side removable covering sheet 1460 covers the non-electrode adhesive hub 1470 in centre and the electrode members (1400, 1420, 1430, 1440, 1450). The device-side removable covering sheet 1460 may also include apertures 1490 (best shown in FIG. 6(B)) that are arranged to allow the conductive electrode connectors 470 of the medical electrodes to pass through the device-side removable covering sheet 1460. This prevents the protruding electrode connectors 470 from pushing against the device-side removable covering sheet 1460 and either damaging or prematurely removing said sheet.

The electrode assembly 1400 is adapted to attach to a medical device by combination of (i) the conductive connectors (in this example press stud 470) of the medical electrode members, (ii) the adhesive flexible seal provided to the device-side of each medical electrode and (iii) the non-electrode adhesive hub 1470 in centre.

Further, the electrode assembly 1400 is adapted to attach to the patient's skin by combination of the medical electrode members (1400, 1420, 1430, 1440, 1450) and the non-electrode adhesive hub 1470 in its centre. The non-electrode adhesive hub 1470 in the centre facilitates positioning the medical device and supporting the weight of the medical device on attachment. In this example, the non-electrode adhesive hub has a square-shaped hole in its centre.

In this example, the flexible layer 420 is a clear plastic film that includes the patient-side adhesive layer 430. Further, the device-side flexible adhesive seal 480 is a foam seal including a device-side adhesive layer to adhere the medical electrodes (1400, 1420, 1430, 1440, 1450) to the device and another adhesive layer to adhere the device-side flexible adhesive seal 480 to the substrate 410. The distance between an inner and outer radii of the device-side flexible adhesive seal 480 may vary to provide seals of different thickness. For example, as shown in FIG. 14(C) the distance between the inner and outer radii of the device-side flexible adhesive seal 480 is larger than the distance between the inner and outer radii of the device-side flexible adhesive seal 480 provided in FIG. 9. The device-side flexible adhesive seal 480 is arranged sit around the electrode connector 470 of each of the medical electrode members (1400, 1420, 1430, 1440, 1450) to facilitate positioning and holding the medical device, reducing movement artefacts, and preventing fluid ingress.

In an embodiment, the adhesive that is used to adhere the electrode assembly 100 to the medical device may be different from the adhesive that is used to adhere the electrode assembly 100 to the patient. For example, the adhesive layer provided to the device-side flexible adhesive seal 480 to connect the medical electrode to the medical device may include an adhesive with a stronger bonding capacity (i.e. be stronger, sticker, more adhesive) relative to the patient-side adhesive layer 430 used to adhere the electrode assembly to the patient. Further, the material and material properties of the flexible layer 420 and the device-side flexible adhesive seal 480 may be varied in order to accommodate variations in the strengths or types of adhesives. In the example shown, the flexible layer 420 may be formed of thermoplastic polyurethane and the device-side flexible adhesive seal 480 may be formed of foam.

Although a preferred embodiment has been described in detail, it should be understood that modifications, changes, substitutions or alterations will be apparent to those skilled in the art without departing from the scope of the present invention as defined in the claims.

Optional embodiments may also be said to broadly include the parts, elements, steps and/or features referred to or indicated herein, individually or in any combination of two or more of the parts, elements, steps and/or features, and wherein specific integers are mentioned which have known equivalents in the art to which the invention relates, such known equivalents are deemed to be incorporated herein as if individually set forth. Accordingly, many modifications will be apparent to those skilled in the art without departing from the scope of the present invention as defined in the claims.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprised", "comprises" or "comprising", will be understood to imply the inclusion of a stated integer or step or group of integers or steps but not the exclusion of any other integer or step or group of integers or steps.

As used herein, a, an, the, at least one, and one or more are used interchangeably, and refer to one or to more than one (i.e. at least one) of the grammatical object. By way of example, "an element" means one element, at least one element, or one or more elements.

In the context of this specification, the term "about" is understood to refer to a range of numbers that a person of skill in the art would consider equivalent to the recited value in the context of achieving the same function or result.

The invention claimed is:

1. An electrode assembly including:
   a plurality of medical electrode members; and
   at least two covering sheets removably attached to the plurality of medical electrode members, wherein the at least two covering sheets include:
     a first covering sheet removably attached to one side of each of the plurality of medical electrode members; and
     a second covering sheet removably attached to an opposite side of each of the plurality of medical electrode members,
     wherein one of the at least two covering sheets holds a first of the plurality of medical electrode members in a predetermined position relative to a second of the plurality of medical electrode members; and
     each of the plurality of medical electrode members has a connector for connecting to a corresponding medical electrode connecting portion on a medical device.

2. The electrode assembly of claim 1, wherein the at least two covering sheets are made of flexible material.

3. The electrode assembly of claim 2, wherein the flexible material of the first covering sheet is different from the flexible material of the second covering sheet.

4. The electrode assembly of claim 3, wherein each of the plurality of medical electrode members includes a first adhesive layer removably attached to the first covering sheet and a second adhesive layer removably attached to the second covering sheet.

5. The electrode assembly of claim 4, wherein the first adhesive layer has different adhesive properties to that of the second adhesive layer.

6. The electrode assembly of claim 1, wherein the relative positions of the plurality of medical electrode members on the at least two covering sheets corresponds to the relative positions of the plurality of electrode connecting portions of the medical device.

7. The electrode assembly of claim 1, further comprising a non-electrode adhesive pad for holding the medical device, wherein the at least two covering sheets are also removably attached to the adhesive pad.

8. The electrode assembly of claim 7, wherein the non-electrode adhesive pad may be arranged to form a shape selected from the group of: a circle, ellipse, triangle, square, rectangle, rhombus, trapezoid, rounded triangle, rounded square, rounded rectangle, rounded rhombus, rounded trapezoid or an irregular shape.

9. The electrode assembly of claim 8, wherein the non-electrode adhesive pad may include an aperture arranged to form a shape selected from the group of: a circle, ellipse, triangle, square, rectangle, rhombus, trapezoid, rounded triangle, rounded square, rounded rectangle, rounded rhombus, rounded trapezoid or an irregular shape.

10. The electrode assembly of claim 8, wherein the non-electrode adhesive pad is located at or proximate to a center of the at least two covering sheets.

11. The electrode assembly of claim 7, wherein a device-side of the non-electrode adhesive pad is spaced apart from each of the plurality of medical electrode members.

12. The electrode assembly of claim 1, wherein the at least one covering sheet includes at least one perforated section.

\* \* \* \* \*